(12) United States Patent
Lee et al.

(10) Patent No.: US 7,632,578 B2
(45) Date of Patent: Dec. 15, 2009

(54) EMITTING COMPOUND FOR ORGANIC ELECTROLUMINESCENT DEVICE AND ORGANIC ELECTROLUMINESCENT DEVICE USING THE SAME

(75) Inventors: Seok-Jong Lee, Suwon-si (KR); Yong-Joong Choi, Yongin-si (KR)

(73) Assignee: Samsung Mobile Display Co., Ltd., Yongin (KR)

( * ) Notice: Subject to any disclaimer, the term of this patent is extended or adjusted under 35 U.S.C. 154(b) by 348 days.

(21) Appl. No.: 10/770,445

(22) Filed: Feb. 4, 2004

(65) Prior Publication Data

US 2004/0157084 A1 Aug. 12, 2004

(30) Foreign Application Priority Data

Feb. 7, 2003 (KR) .................. 10-2003-0007933

(51) Int. Cl.
*H01J 1/62* (2006.01)
*C07D 235/00* (2006.01)
*C07D 221/02* (2006.01)
*C07D 401/00* (2006.01)

(52) U.S. Cl. .................. 428/690; 428/917; 313/504; 313/506; 548/304.4; 548/302.1; 548/309.7; 546/118; 546/273.1

(58) Field of Classification Search ............ 252/301.16; 428/690, 917; 313/503, 504, 506; 257/40, 257/102, 103; 548/304.4

See application file for complete search history.

(56) References Cited

U.S. PATENT DOCUMENTS 5,141,671 A 8/1992 Bryan et al. ........... 252/301.16

(Continued)

FOREIGN PATENT DOCUMENTS

CN 1186492 A 7/1998

(Continued)

OTHER PUBLICATIONS

Office Action issued in Chinese Patent Application No. 200410043031.1 on Jul. 29, 2005.

(Continued)

*Primary Examiner*—D. Lawrence Tarazano
*Assistant Examiner*—Camie S Thompson
(74) *Attorney, Agent, or Firm*—Stein McEwen, LLP

(57) ABSTRACT

An emitting compound for an organic electroluminescent device, and an organic electroluminescent device using the same, supply an effective luminance, an efficient driving voltage, and color purity. The emitting compound has an imidazopyridine frame represented as in the following Formula 1:

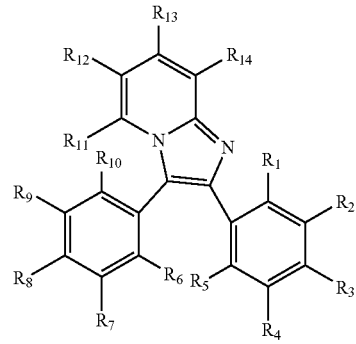

where $R_1$ to $R_{14}$, each of which is independent, refer to the functional groups recited herein.

8 Claims, 15 Drawing Sheets

U.S. PATENT DOCUMENTS

| | | |
|---|---|---|
| 6,998,487 B2 * | 2/2006 | Kim et al. .................... 546/15 |
| 2005/0079387 A1 * | 4/2005 | Lee et al. .................... 428/690 |

FOREIGN PATENT DOCUMENTS

| | | |
|---|---|---|
| JP | 2001-6877 | 1/2001 |
| JP | 2001-006877 | 1/2001 |
| JP | 2001-035664 | 2/2001 |
| JP | 2001-357977 | 12/2001 |
| JP | 2002-515461 | 5/2002 |
| WO | WO 96/31509 | 10/1996 |
| WO | WO 99/59635 | 11/1999 |
| WO | WO 02/20459 A1 | 3/2002 |
| WO | WO 02/20460 A1 | 3/2002 |
| WO | WO 02/088274 | 11/2002 |

OTHER PUBLICATIONS

"Search Strategy (CAN)(133:362730)", (American Chemical Society 2000).
Partial CN 1186492 (including Abstract and pp. 1 and 15-22).
Partial JP 2002-515461 (including Abstract and pp. 1 and 4).
Office Action issued in Korean Patent Application No. 2003-7933 on Jan. 31, 2006.

* cited by examiner

EMITTING COMPOUND FOR ORGANIC ELECTROLUMINESCENT DEVICE AND ORGANIC ELECTROLUMINESCENT DEVICE USING THE SAME

CROSS-REFERENCE TO RELATED APPLICATIONS

This application claims the benefit of Korean Patent Application No. 2003-7933, filed on Feb. 7, 2003, the disclosure of which is hereby incorporated herein by reference in its entirety.

BACKGROUND OF THE INVENTION

1. Field of the Invention

The present invention relates to a light emitting compound for an organic electroluminescent device and an organic electroluminescent device using the same, and more particularly, to a light emitting compound used in an organic electroluminescent device that is a self-emission type display device and has a wide viewing angle, an effective contrast and a fast response time, and an organic electroluminescent device using the emitting compound.

2. Description of the Related Art

An organic electroluminescent (hereinafter referred to as "EL") device has advantages in that the viewing angle is wide, the contrast is significant, and the response time is as fast as a self-emission type display device.

An EL device is divided into an inorganic EL device and an organic EL device depending on materials to form an emitting layer, wherein the organic EL device has advantages in that the luminance, the driving voltage and the response speed characteristics are improved compared to the such characteristics of the inorganic EL device, and the organic EL device is displayed in multi-colors.

An ordinary organic EL device has a structure in which the anode is formed on an upper part of the substrate, and the hole transport layer, the emitting layer, the electron transport layer and the cathode are sequentially formed on an upper part of the anode, wherein the hole transport layer, the emitting layer and the electron transport layer are organic thin films formed from organic compounds.

The driving principle of an organic EL device having the foregoing structure is as follows.

If a voltage is applied between the anode and the cathode, the holes injected from the anode are transferred to the emitting layer via the hole transport layer. On the other hand, electrons are injected into the emitting layer from the cathode via the electron transport layer, and carriers are recombined in the emitting layer region to produce an exciton. The exciton is changed from the excited state to the ground state, emitting fluorescence from the emitting layer accordingly so that an image is formed.

On the other hand, although compounds such as diphenylanthracene, tetraphenylbutadiene and a distyrylbenzene derivative have recently been developed as a blue emitting material, and the IDEMITSU CORPORATION has recently developed a styryl compound (PCT/JP2001/7295) and an arylamine compound (PCT/JP2001/7477) as a blue emitting material, the blue emitting materials have disadvantages in that the color purity is low, and the life time is decreased due to a lower thin film stability.

Although, as disclosed in U.S. Pat. No. 5,141,671, the EASTMAN KODAK CORPORATION developed Balq, which is an aluminum complex, as a blue emitting material in 1992, Balq is now used as a hole blocking layer rather than a blue emitting material due to its ineffective emission efficiency and color coordinates (0.18, 0.27). Therefore, there is a need to develop a blue emitting material having high heat resistance, emission efficiency and color purity.

SUMMARY OF THE INVENTION

Therefore, to solve the foregoing and/or other disadvantages, it is an aspect of the present invention to provide an emitting compound for an organic electroluminescent device having an effective luminance, an efficient driving voltage and color purity, and an organic electroluminescent device using the emitting compound.

To achieve the foregoing and/or other aspects, the present invention provides an emitting compound characterized in that it has an imidazo-pyridine frame represented as in the following Formula 1:

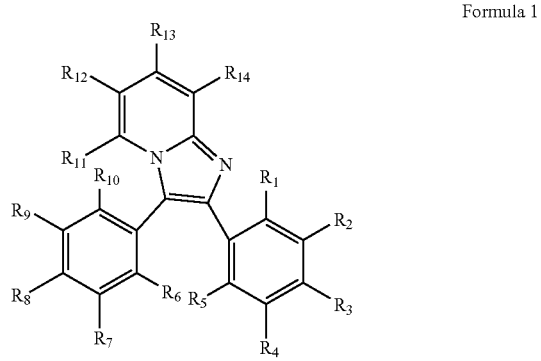

Formula 1 where $R_1$ to $R_{14}$, each of which is independent, are each one functional group selected from the group consisting of a hydrogen atom, a halogen atom, a substituted or a non-substituted alkyl group having 1 to 30 carbon atoms, a substituted or a non-substituted alkoxy group having 1 to 30 carbon atoms, a substituted or a non-substituted aryl group having 6 to 30 carbon atoms, a substituted or a non-substituted aryloxy group having 6 to 30 carbon atoms, a substituted or a non-substituted heterocyclic group having 6 to 30 carbon atoms, a substituted or a non-substituted condensation polycyclic group having 6 to 30 carbon atoms, a substituted or a non-substituted heterocyclic group having 5 to 30 carbon atoms, an amino group, an arylamino group having 6 to 30 carbon atoms, a cyano group, a nitro group, a hydroxy group, a halogen atom, and an aryl and an alkyl sufone group having 6 to 30 carbon atoms, wherein adjacent groups are bonded to each other to form a saturated or a nonsaturated carbon ring.

Additional aspects and/or advantages of the invention will be set forth in part in the description which follows and, in part, will be obvious from the description, or may be learned by practice of the invention.

BRIEF DESCRIPTION OF THE DRAWINGS

These and/or other aspects and advantages of the invention will become apparent and more readily appreciated from the following description of the embodiments, taken in conjunction with the accompanying drawings of which.

DETAILED DESCRIPTION OF THE EMBODIMENTS

Figure 1:
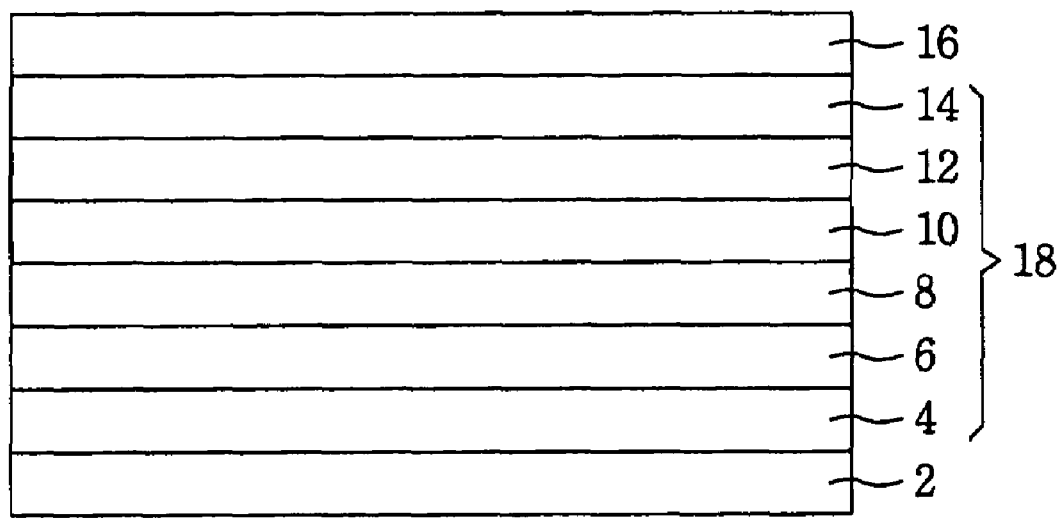
FIG. 1 is a cross sectional view to show a schematic lamination structure of an organic electroluminescent device according to one typical embodiment of the present invention.

Reference will now be made in detail to the embodiments of the present invention, examples of which are illustrated in the accompanying drawings, wherein like reference numerals refer to the like elements throughout. The embodiments are described below to explain the present invention by referring to the figures.

An organic electroluminescent device of the present invention comprises a pair of electrodes and an organic compound layer comprising one or more layers and having an emitting layer positioned between the electrodes and represented as in the following Formula 1.

First, an anode electrode is formed by coating a material for the anode electrode on an upper part of the substrate, wherein a substrate used in an organic EL device, such as an organic EL device substrate that is known to those skilled in the art, is used as the substrate, and a glass substrate or a transparent plastic substrate having superior transparency, surface flatness, handling easiness and a waterproofing property is preferably used. Indium tin oxide (ITO), indium zinc oxide (IZO), tin dioxide ($SnO_2$) and zinc oxide (ZnO), which are transparent and have superior conductivity, are examples of the material used for the anode electrode.

An organic compound layer comprising at least one or more layers, including a patterned emitting layer, is formed on an upper part of the anode electrode.

A compound of the following Formula 1, which has an imidazo-pyridine frame, is used alone as a light-emitting layer material or as a host of the light-emitting layer material, and a blue phosphorescent or fluorescent dopant is used as the dopant by a vacuum thermal deposition method, as is known to those skilled in the art, when the dopant is used. A doping concentration is not particularly limited, iridiumtris(phenylpyridine) (Irppy3) is used as a phosphorescent dopant, and IDE102 (manufactured by IDEMITSU CORPORATION) is used as a fluorescent dopant.

Formula 1

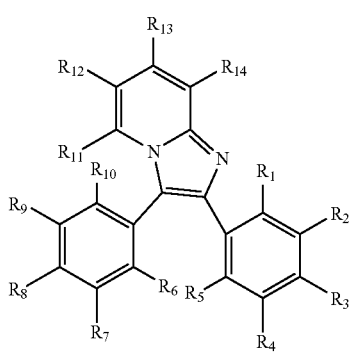

where $R_1$ to $R_{14}$, each of which is independent, are each one functional group selected from the group consisting of a hydrogen atom, a halogen atom, a substituted or a non-substituted alkyl group having 1 to 30 carbon atoms, a substituted or a non-substituted alkoxy group having 1 to 30 carbon atoms, a substituted or a non-substituted aryl group having 6 to 30 carbon atoms, a substituted or a non-substituted aryloxy group having 6 to 30 carbon atoms, a substituted or a non-substituted heterocyclic group having 6 to 30 carbon atoms, a substituted or a non-substituted condensation polycyclic group having 6 to 30 carbon atoms, a substituted or a non-substituted heterocyclic group having 5 to 30 carbon atoms, an amino group, an arylamino group having 6 to 30 carbon atoms, a cyano group, a nitro group, a hydroxy group, a halogen atom, and an aryl and an alkyl sufone group having 6 to 30 carbon atoms, wherein adjacent groups are bonded to each other to form a saturated or a nonsaturated carbon ring.

A compound of Formula 1 is preferably one compound selected from the group consisting of the following Formulas 2 to 31.

Formula 2

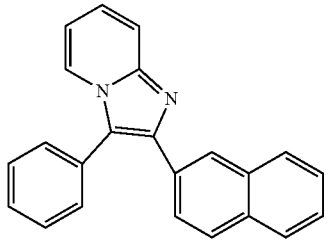

Formula 3

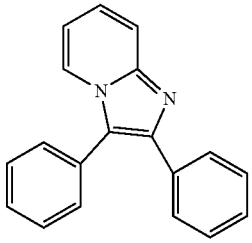

Formula 4

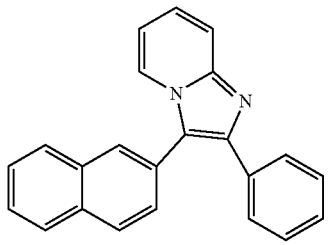

Formula 5

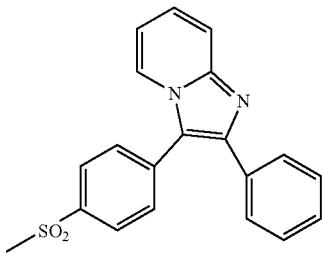

Formula 6

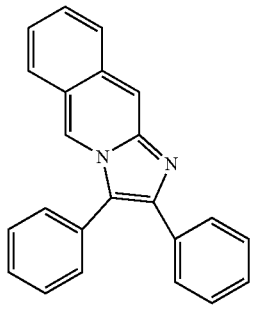

Formula 7

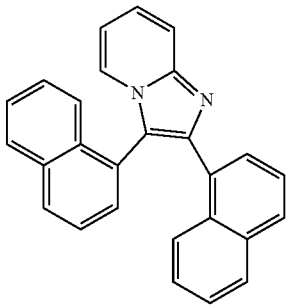

-continued
Formula 8
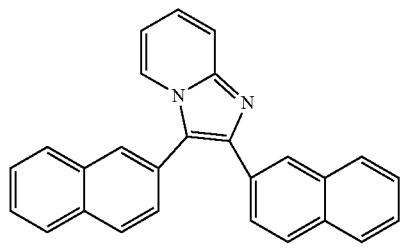
Formula 9
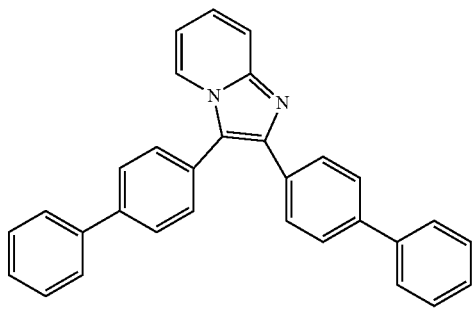
Formula 10
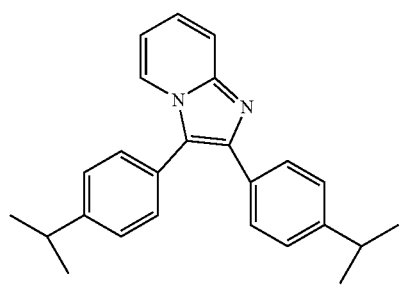
Formula 11
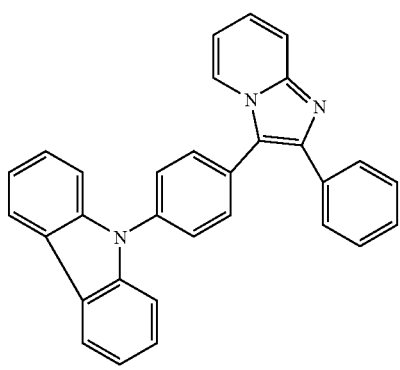
Formula 12
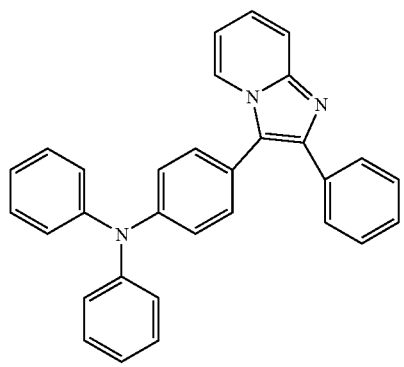
Formula 13
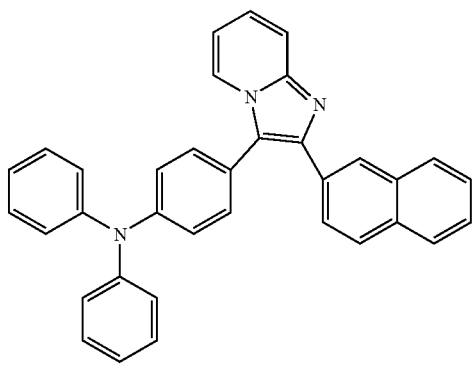
Formula 14
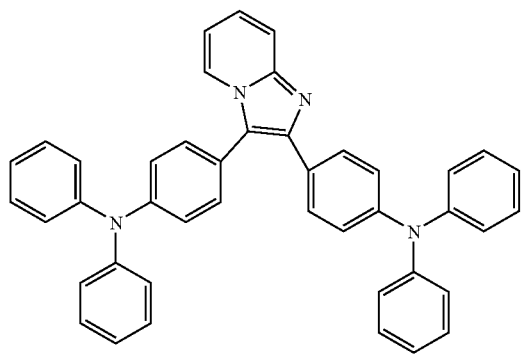
Formula 15
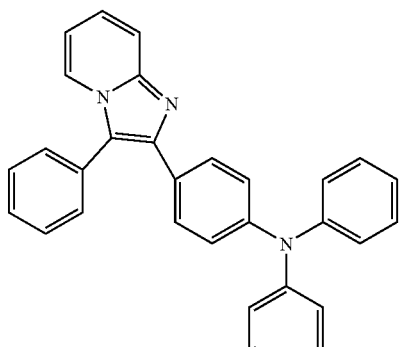

-continued
Formula 16
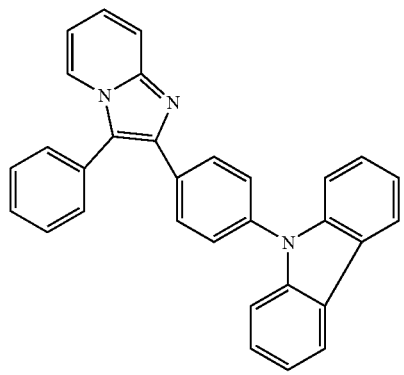
Formula 17
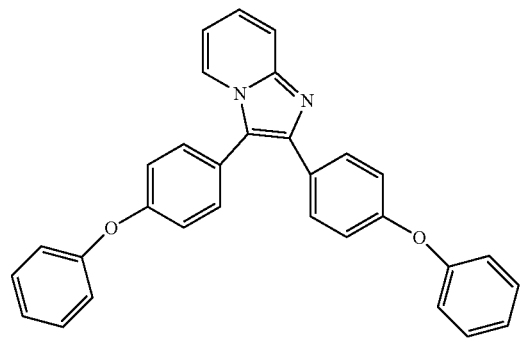
Formula 18
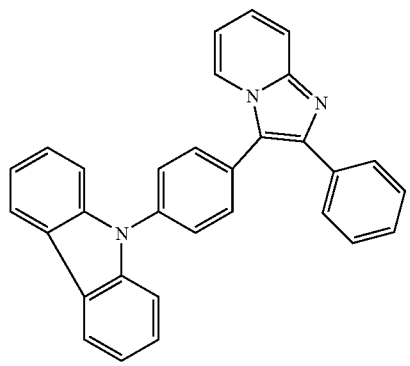
Formula 19
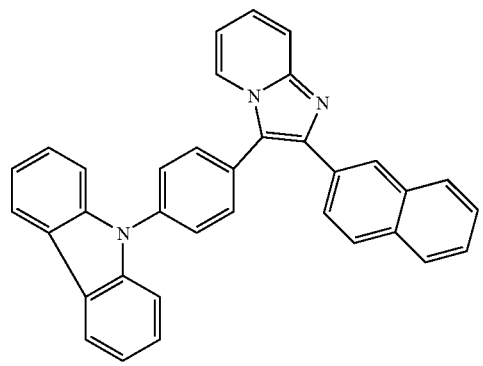
Formula 20
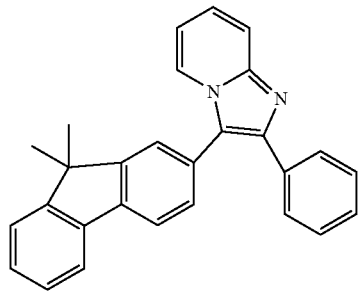
Formula 21
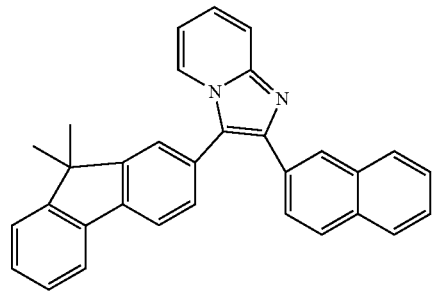
Formula 22
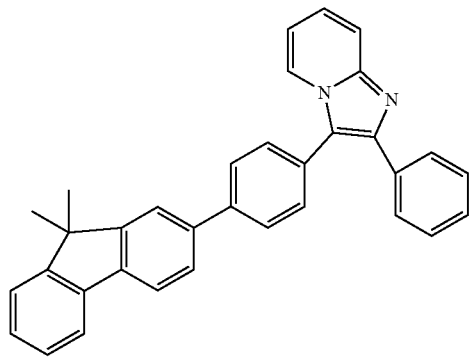
Formula 23
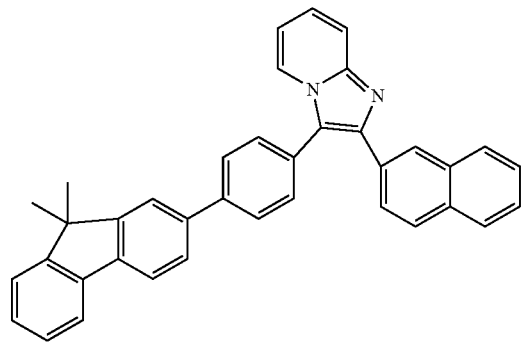

-continued
Formula 24
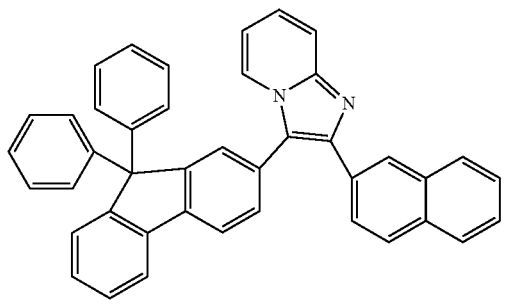
Formula 25
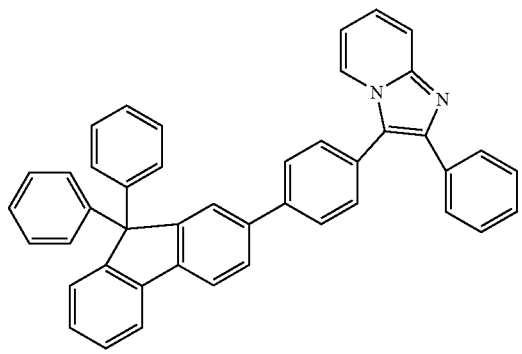
Formula 26
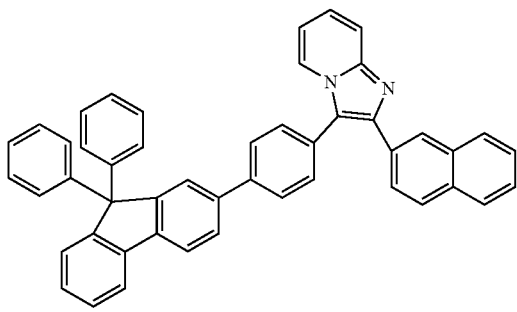
Formula 27
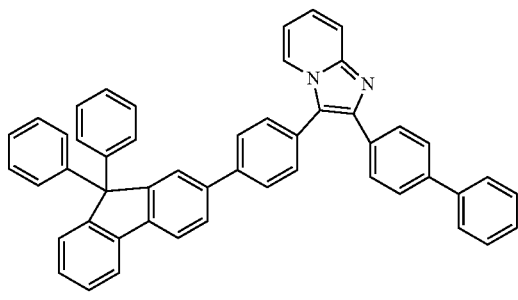
Formula 28
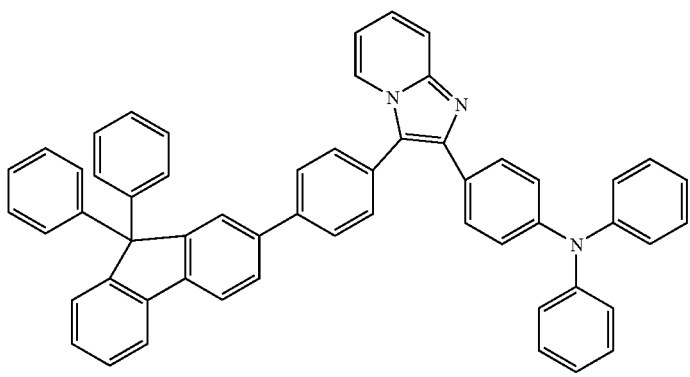
Formula 29
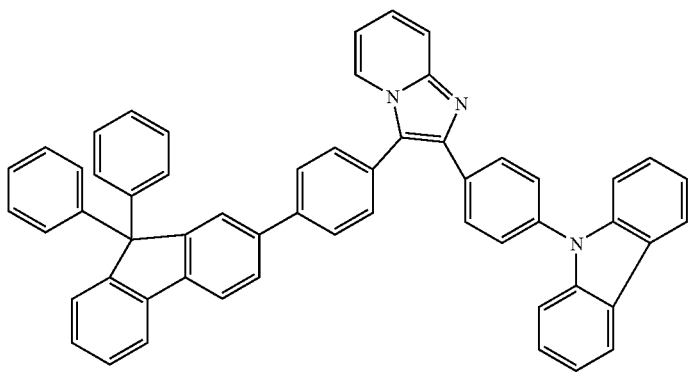

Formula 30

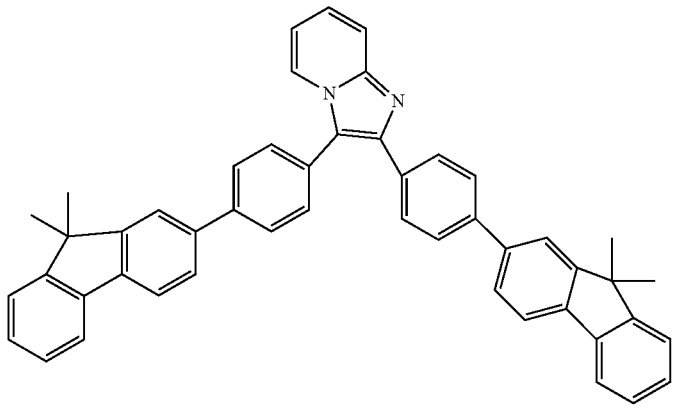

Formula 31

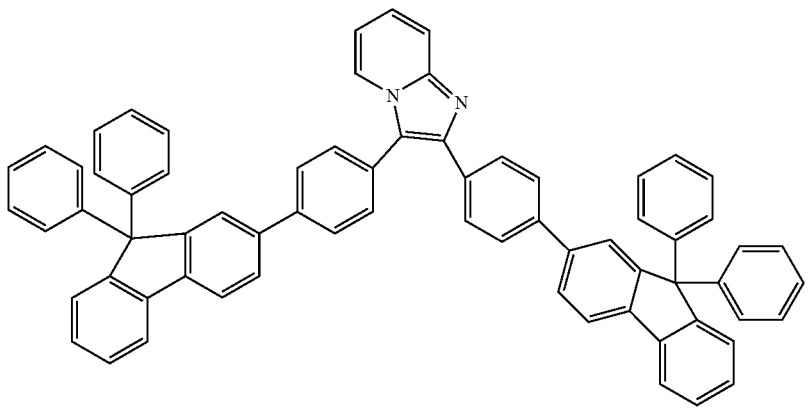

A more preferable emitting layer material is one material selected from the Formulas 1, 2, 4, 18, 19, 20, 21, 22, 24 and 25.

A compound used as the emitting layer may be used as a blue emitting compound.

Methods known to those skilled in the art, such as vacuum deposition, spin coating, laser deposition, and the like may be used as a method to form the emitting layer, and laser induced thermal imaging (LITI) may preferably be used to reduce mis-alignment of the emitting layer.

Then, an organic EL device is completed by vacuum thermal depositing a cathode forming metal on an upper part of the organic compound layer, thus forming a cathode electrode, wherein the cathode forming metal includes at least one of Li, Mg, Al, Al—Li, Ca, Mg—In, Mg—Ag, and the like.

The organic compound layer further comprises one or more layers selected from the group consisting of the hole injection layer, the hole transport layer, the electron injection layer and the electron transport layer, in addition to the emitting layer.

FIG. 1 is a cross sectional view to show a structure of an organic electroluminescent device in which one or more organic film layers are further contained in the organic compound layer in addition to the emitting layer according to one typical embodiment of the present invention.

The substrate 2 and the anode electrode 4 are formed in the same manner as described above.

The hole injection layer 6 is generally formed on an upper part of the anode electrode by vacuum thermal deposition or a spin coating method. A material to form the hole injection layer 6 is not particularly limited, and CuPc or starburst type amines including TCTA, m-MTDATA and m-MTDAPB may be used as the hole injection layer.

The transport layer 8 is formed on an upper part of the hole injection layer by vacuum thermal deposition or a spin coating method. A material to form the hole transport layer 8 is not particularly limited, but may include N,N'-bis(3-methylphenyl)-N,N'-diphenyl--4,4'-diamine(TPD), N,N'-di(naphthalene-1-yl)-N,N'-diphenyl benzidine and/or N,N'-di(naphthalene-1-yl)-N,N'-diphenyl benzidine(α-NPD).

Subsequently, an emitting layer 10 is introduced onto an upper part of the hole transport layer 8 by vacuum deposition, spin coating and laser deposition methods, and laser induced thermal imaging (LITI) is generally used to reduce misalignment of the emitting layer. A compound represented as in Formula 1 is used as the emitting layer 10 as described above, and one compound selected from the group consisting of the foregoing Formulas 2 to 31 is typically used as the emitting layer 10.

Furthermore, an electron transport layer 12 is formed by vacuum deposition or spin coating a thin film on the emitting layer 10. Alq3 is used as a material to form the electron transport layer 12. Furthermore, an electron injection layer 14 may be disposed on the electron transport layer 12, and the electron injection layer 14 is not particularly limited to a certain material. Such materials as LiF, CsF, Li$_2$O and BaO are used as the electron injection layer 14.

An organic EL device is completed by vacuum thermal depositing a cathode forming metal on an upper part of the organic compound layer 18, thus forming a cathode electrode, wherein the cathode forming metal includes at least one of Li, Mg, Al, Al—Li, Ca, Mg—In, Mg—Ag, and the like.

Furthermore, an organic electroluminescent device of the present invention further selectably comprises one or two layers of an intermediate layer in addition to the anode electrode, the hole injection layer, the hole transport layer, the emitting layer, the electron transport layer, the electron injection layer and the cathode electrode.

Typical examples of the present invention are as follows. However, the following examples are provided only to help understand the present invention, and the present invention is not limited to the following examples.

SYNTHESIS EXAMPLE 1 (PREPARATION OF THE COMPOUND OF FORMULA 2)

A compound represented as in Formula 2 was synthesized along the reaction path of chemical Reaction Formula 1.

Formula 2

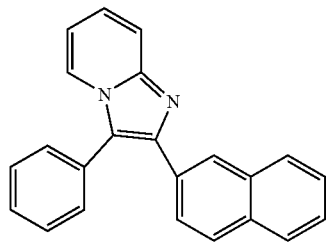

Reaction Formula 1

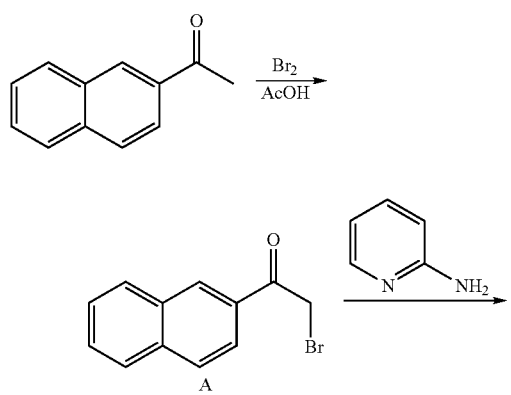

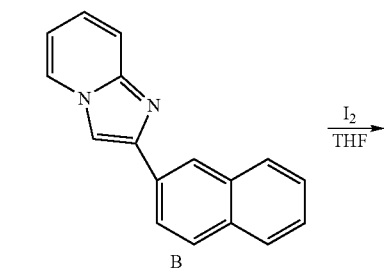

-continued

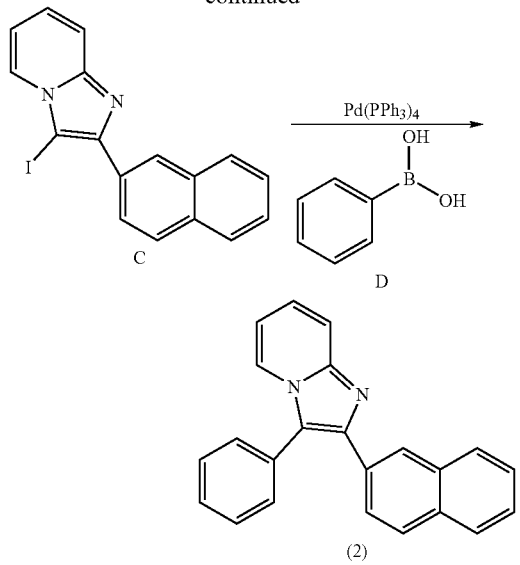

Synthesis of Intermediate A

The solution was cooled to 0° C. after dissolving 17 g (100 mmol) of acetylnaphthalene into 300 ml of $CCl_4$, and a catalytic amount of anhydrous hydrogen chloride was added to the cooled solution. After adding 100 mmol of $Br_2$ to the solution, the mixed solution was agitated at 0° C. and then agitated at room temperature for 3 hours so that the color of the bromine was completely removed. The mixed solution was washed several times by adding ice water to the mixed solution after the color of the bromine was completely removed. A coarse product was obtained by reduced pressure drying the dried $CCl_4$ layer after drying a washed $CCl_4$ layer using $MgSO_4$. 19.9 g (a yield of 90%) of the solid phase intermediate A was obtained by recrystallizing the coarse product using hexane.

Synthesis of Intermediate B

The mixed solution (see preceding paragraph) was agitated at room temperature for 5 hours after dissolving 12.5 g (50 mmol) of intermediate A into 250 ml of DME and adding 4.7 g (50 mmol) of 2-aminopyridine to the dissolved solution in the solid state. The agitated solution was refluxed for 12 hours to provide a solvent removed solution. 250 ml of dichloromethane was added to the solvent removed solution so that dichloromethane was dissolved into the solvent removed solution after removing the solvent by reduced pressure distilling the refluxed solution. The pH of the dichloromethane-dissolved solution was adjusted to 10 using a 10% sodium carbonate solution. The remaining aqueous solution layer was extracted twice using 200 ml of dichloromethane after separating the dichloromethane layer from the aqueous solution layer in the pH adjusted solution. 7.9 g (a yield of 65%) of intermediate B was obtained by separation refining the obtained residue using silica gel pipe chromatography after obtaining a residue by drying the collected organic layer using magnesium sulfate and an evaporating solvent.

Synthesis of Intermediate C 3.7 g (15 mmol) of intermediate B was dissolved into 30 ml of pyridine, 5.7 g (22.5 mmol) of iodine was added to the solution, and the iodine added solution was agitated at 50° C. for 5 hours. The resulting solution was extracted three times using 250 ml of dichloromethane after stopping the reaction of the solution using a saturated oxalic acid solution. 3.2 g (a yield of 57%) of intermediate C was obtained by separation refining the obtained residue using silica gel pipe chromatography after obtaining a residue by drying the collected organic layer using magnesium sulfate and an evaporating solvent.

Synthesis of Intermediate D

A reaction solution was prepared by dissolving 2.1 ml (20 mmol) of bromobenzene into 100 ml of THF, adding 13 ml (21 mmol) of 1.6 mol n-butyllithium dissolved in n-hexane at −78° C. to the solution, and agitating the mixed solution for 2 hours. The mixed solution was agitated at −78° C. for 3 hours and agitated at room temperature for 12 hours by putting the prepared solution into the reaction solution after preparing a solution by adding 3.4 ml (30 mmol) of trimethylborate to 50 ml of THF in another flask and cooling the solution to −78° C. The resulting solution was agitated at room temperature for 2 hours after injecting 12 moles of hydrochloric acid aqueous solution into the agitated solution. The resulting solution was extracted three times using 100 ml of diethyl ether after adjusting the pH of the solution to strongly basic using a 4 M NaOH aqueous solution. 1.6 g (a yield of 65%) of white solid intermediate D was obtained by recrystallizing the obtained residue using n-hexane after obtaining a residue by drying the collected organic layer using magnesium sulfate and an evaporating solvent.

Synthesis of Compound of Formula 2

Figure 2:
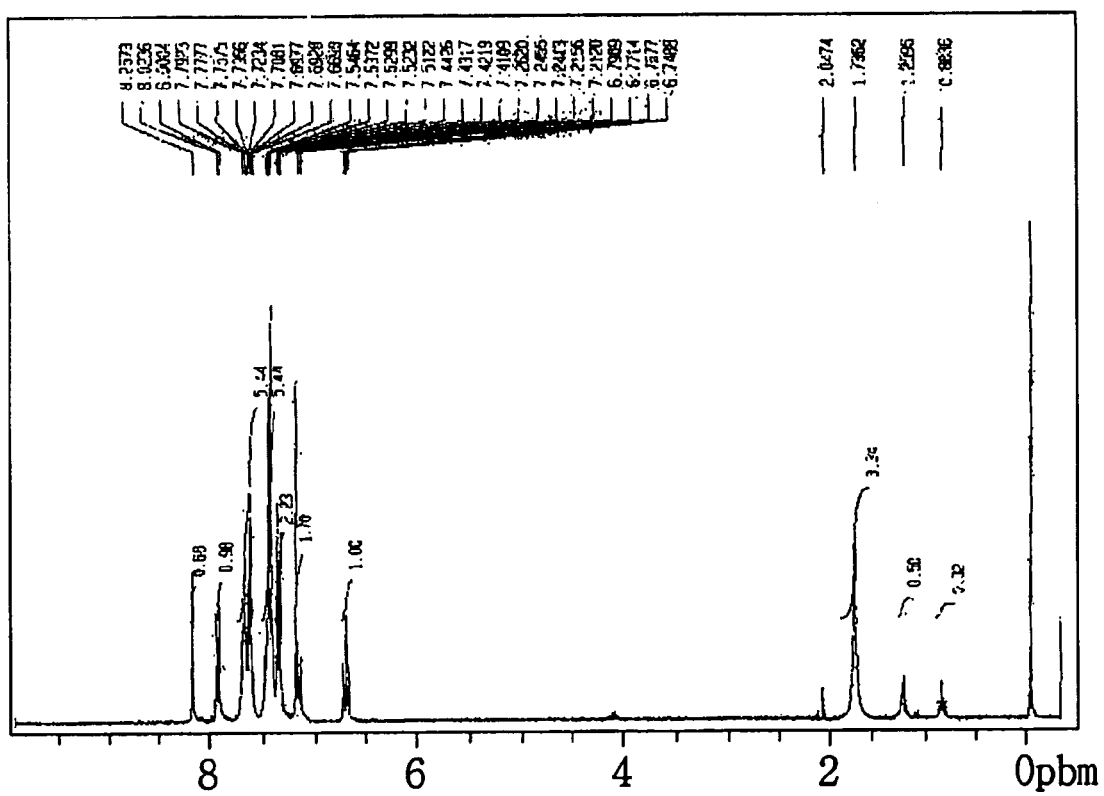
FIG. 2 is $^1$H NMR spectrum to confirm a structure in which a light-emitting compound of synthesis example 1 of the present invention is synthesized.

A reaction solution was prepared by dissolving 1.85 g (5 mmol) of intermediate C and 732 mg (6 mmol) of intermediate D into 50 ml of DME, adding 290 mg (0.25 mmol) of tetrakistriphenylphosphinepalladium to the solution, adding an aqueous solution in which 400 mg (10 mmol) of NaOH is dissolved into 20 ml of distilled water to the solution and agitating the resulting solution at 75° C. for 12 hours. The reaction solution was extracted three times using 100 ml of dichloromethane. 1.12 g (a yield of 70%) of a compound of Formula 2 was obtained by separation refining the obtained residue using silica gel pipe chromatography after obtaining a residue by drying the collected organic layer using magnesium sulfate and an evaporating solvent. The structure of the obtained compound was confirmed to be $^1$H NMR as illustrated in FIG. 2. $^1$H NMR (CDCl$_3$, 300 MHz) δ(ppm) 8.26 (s, 1H), 8.02 (d, 1H), 7.79-7.67(m, 5H), 7.54-7.42(m, 7H), 7.21 (dd, 1H), 6.76(dd, 1H).

EXAMPLE 1

ITO having 15 Ω/cm$^2$ (1200 Å) manufactured by CORNING CORPORATION was used as the anode. A glass substrate was cut to a size of 50 mm×50 mm×0.7 mm, and the cut glass substrate was cleaned by ultrasonic waves in isopropyl alcohol and pure water for 5 minutes and cleaned by UV-ozone for 30 minutes before the cleaned glass substrate was used. A hole injection layer was formed to a thickness of 600 Å by vacuum depositing IDE406 (manufactured by IDEMITSU CORPORATION) on an upper part of the substrate. Subsequently, a hole transport layer was formed by vacuum depositing 4,4'-bis biphenyl (hereinafter referred to as "NPB") to a thickness of 300 Å on an upper part of the hole injection layer. An emitting layer was formed to a thickness of 250 Å by vacuum depositing a compound of Formula 2 on an upper part of the hole transport layer after forming the hole transport layer. After forming the emitting layer, an electron transport layer having a thickness of 300 Å was formed by vacuum depositing Alq3 on an upper part of the emitting layer. An organic electroluminescent device was fabricated as illustrated in FIG. 1 by sequentially vacuum depositing LiF having a thickness of 10 Å as the electron injection layer and Al having a thickness of 3,000 Å as the cathode electrode on an upper part of the electron transport layer, thus forming the LiF/Al electrode.

Figure 5:
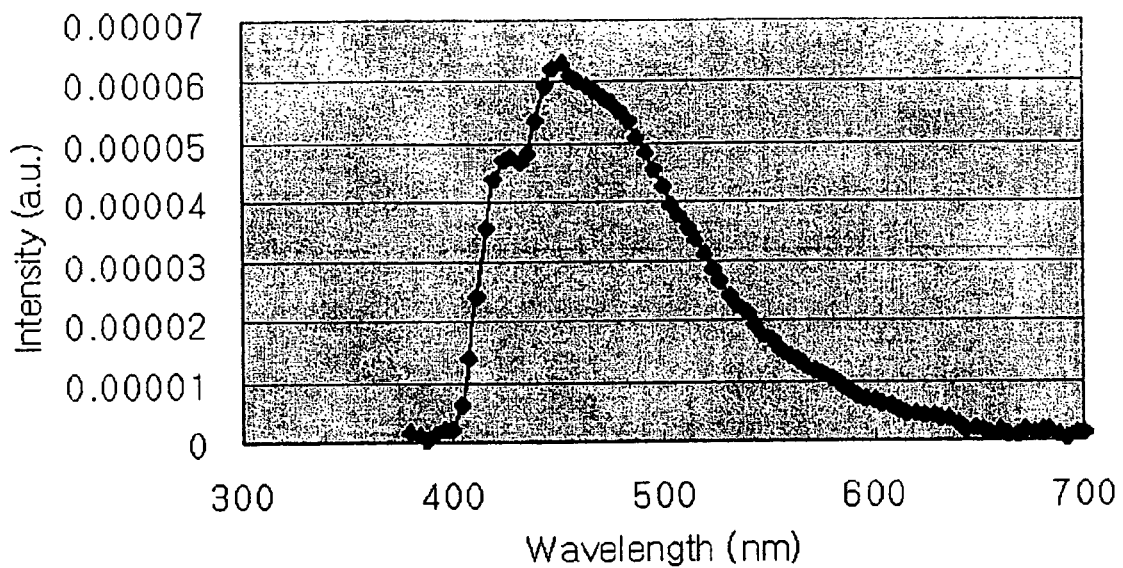
FIG. 5 is an electroluminescence (EL) spectrum obtained by measuring the electroluminescence of the fabricated organic electroluminescent device after fabricating an organic electroluminescent device according to example 1 using a light-emitting compound of the present invention.
Figure 6:
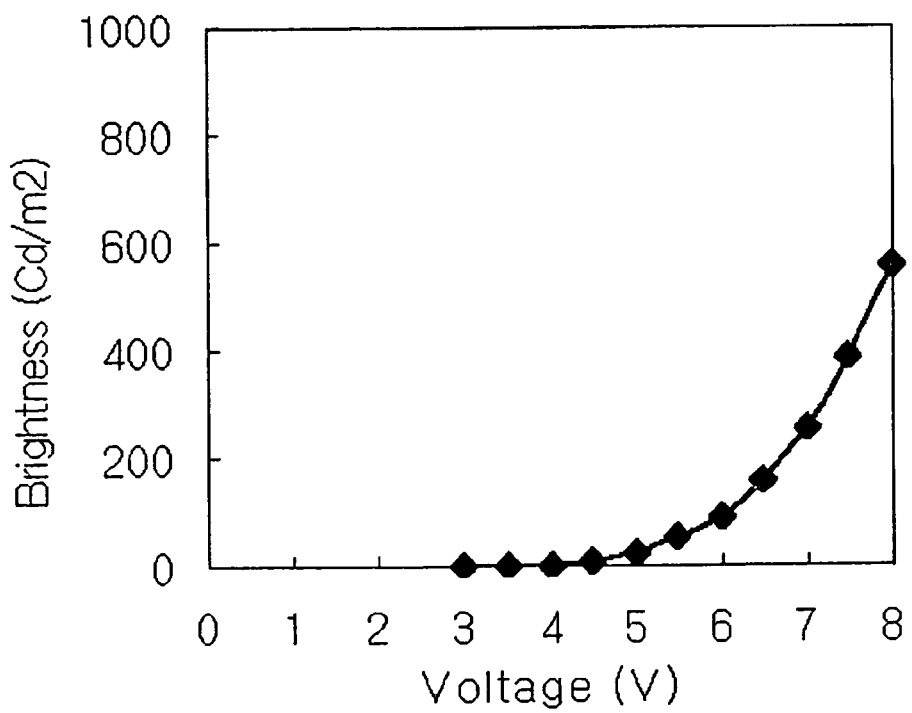
FIG. 6 is a luminance-voltage graph obtained by measuring the luminance and voltage of the fabricated organic electroluminescent device after fabricating an organic electroluminescent device according to example 1 using a light-emitting compound of the present invention.
Figure 7:
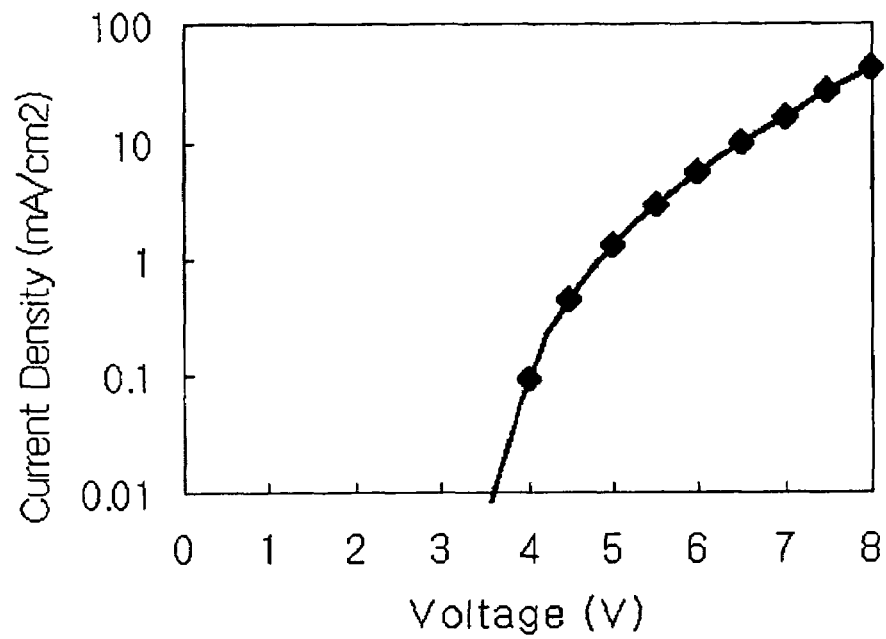
FIG. 7 is a current density-voltage graph obtained by measuring the current density and voltage of the fabricated organic electroluminescent device after fabricating an organic electroluminescent device according to example 1 using a light-emitting compound of the present invention.
Figure 8:
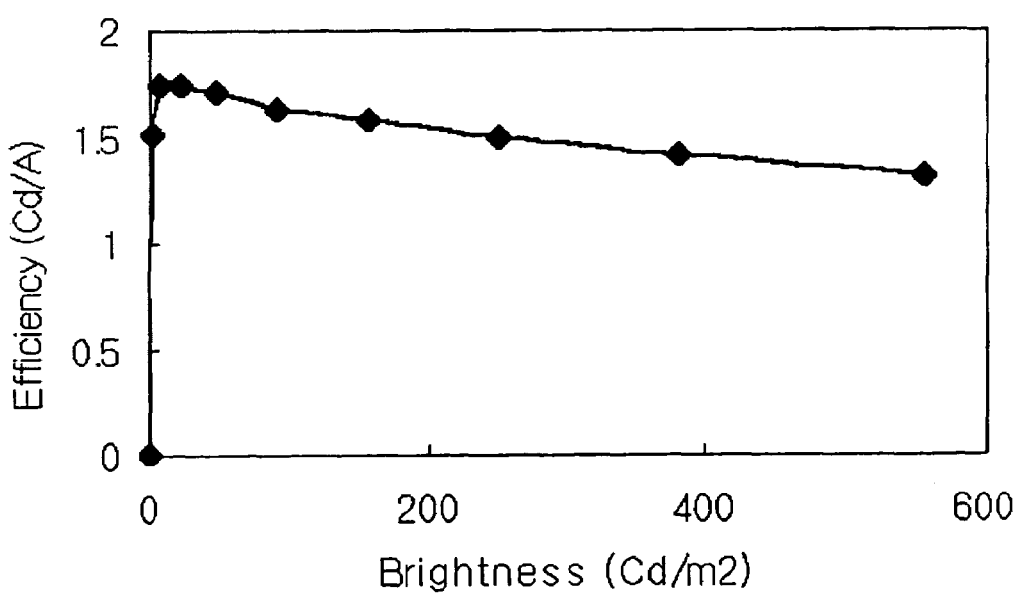
FIG. 8 is an efficiency-luminance graph obtained by measuring the efficiency and luminance of the fabricated organic electroluminescent device after fabricating an organic electroluminescent device according to example 1 using a light-emitting compound of the present invention.

With respect to the characteristics of an organic electroluminescent device, a blue emitting compound whose purity was effective was obtained since the organic electroluminescent device had an emission luminance of 251 cd/m$^2$, an emission efficiency of 1.5 cd/A and color coordinates of 0.17 and 0.18 at a DC voltage of 7 V, as illustrated in FIG. 5 which shows an EL spectrum, FIG. 6 which shows a luminance-voltage graph, FIG. 7 which shows a current density-voltage graph, and FIG. 8 which shows an efficiency-luminance graph.

Figure 3:
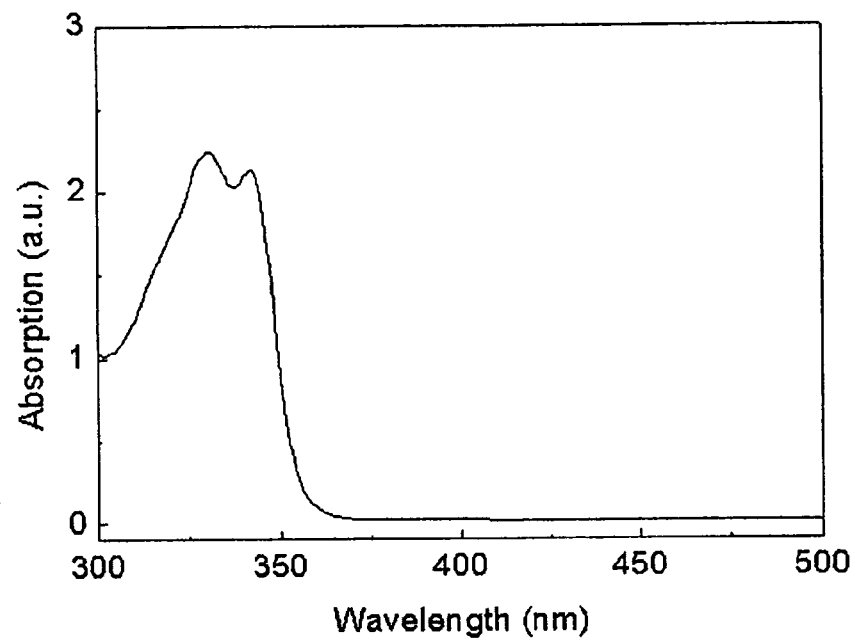
FIG. 3 is an UV absorption spectrum obtained by measuring the formed thin film after forming a light-emitting compound of synthesis example 1 of the present invention in a thin film.
Figure 4:
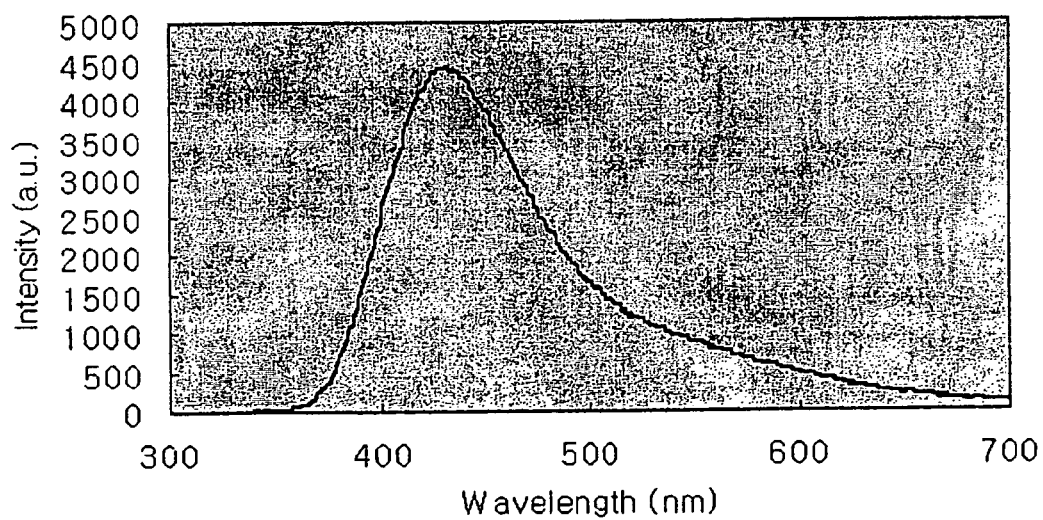
FIG. 4 is a photoluminescence (PL) spectrum of a light-emitting compound of synthesis example 1 of the present invention.

Furthermore, an UV absorption spectrum and a PL spectrum of the thin film were measured after forming a thin film by spin coating a solution prepared by dissolving 1 wt. % of a compound of Formula 2 into toluene on a substrate which was obtained by cutting a glass substrate to a size of 50 mm×50 mm×0.7 mm. The respective measurement results were represented in FIG. 3 and FIG. 4, wherein the UV absorption peaks were 330 and 342 nm, and the maximum PL peak on the PL spectrum was 432 nm. A HOMO energy level of 5.79 eV and a LUMO energy level of 2.61 eV were obtained through the UV absorption spectrum, and UPS (Ultraviolet Photoelectron Spectroscopy), which measures an ionization potential.

SYNTHESIS EXAMPLE 2 (PREPARATION OF COMPOUND OF FORMULA 18)

A compound of Formula 18 was prepared along the reaction path of chemical Reaction Formula 2.

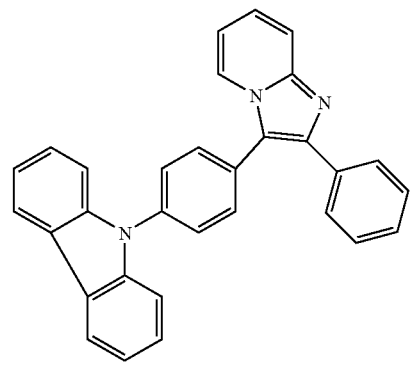

Formula 18

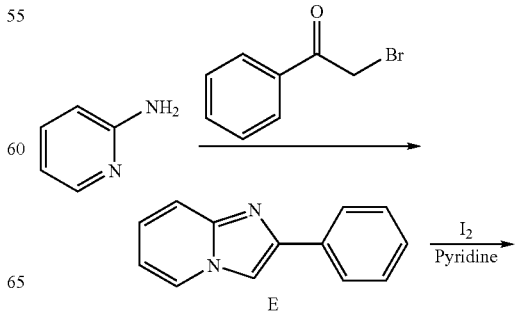

Reaction Formula 2

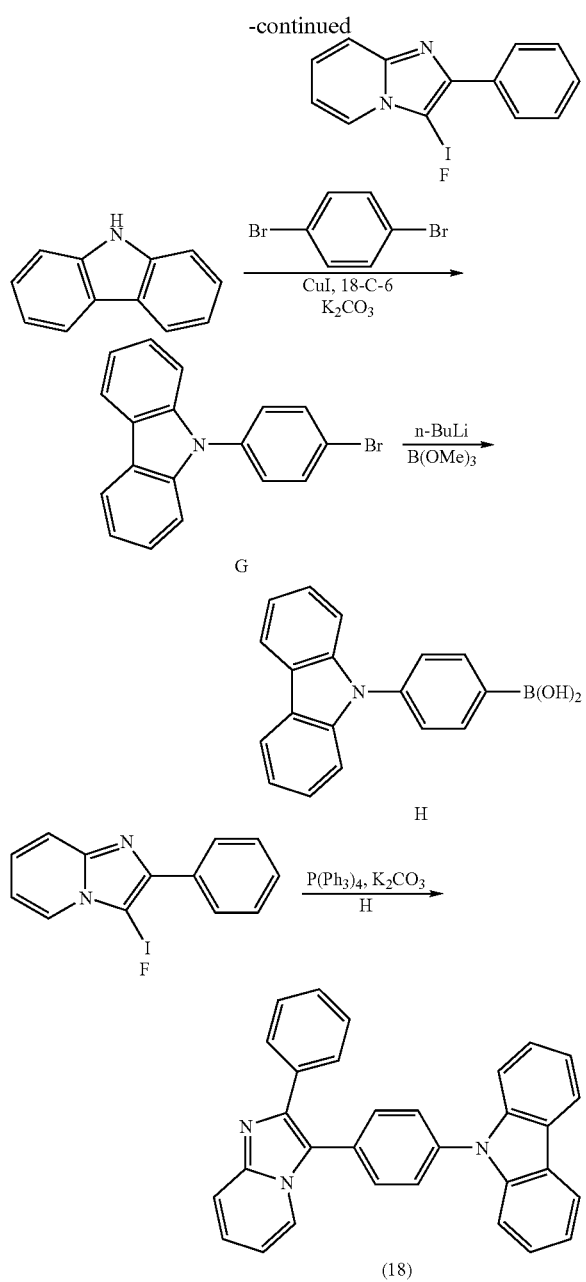

Synthesis of Intermediate E

The agitated solution was refluxed for 12 hours after dissolving 1.99 g (10 mmol) of bromoacetophenone into 50 ml of DME, adding 1 g (10 mmol) of 2-aminopyridine in the solid state to the solution, and agitating the solution at room temperature for 5 hours to provide a solvent removed solution. 60 ml of dichloromethane was added to the solvent removed solution so that dichloromethane was dissolved into the solvent removed solution after removing solvent by reduced pressure distilling the refluxed solution. The pH of the dichloromethane dissolved solution was adjusted to 10 using a 10% sodium carbonate solution. The remaining aqueous solution layer was extracted twice using 50 ml of dichloromethane after separating the dichloromethane layer from the aqueous solution layer in the pH adjusted solution. 1.26 g (a yield of 65%) of intermediate E was obtained by separation refining the obtained residue using silica gel pipe chromatography after obtaining a residue by drying the collected organic layer using magnesium sulfate and an evaporating solvent. $^1$H NMR (CdCl3, 300 MHz)δ(ppm) 8.1(d, 1H), 8.03-7.90(m, 2H), 7.80(d, 1H), 7.60(dd, 1H), 7.51-7.40(m, 2H), 7.39-7.27(m, 1H), 7.21-7.08(m, 1H), 1.43(dd, 1H); 13C NMR (CdCl3, 100 MHz)δ(ppm) 145.7, 145.7, 133.7, 128.7, 128.6, 127.9, 126.0, 124.5, 117.4, 112.3, 108.1.

(2) Synthesis of Intermediate F 400 mg (2 mmol) of intermediate E was dissolved into 10 ml of pyridine, 760 mg (3 mmol) of iodine was added to the solution, and the iodine added solution was agitated at 50° C. for 5 hours. The resulting solution was extracted three times using 10 ml of dichloromethane after stopping the reaction of the solution using a saturated oxalic acid solution. 462 mg (a yield of 72%) of intermediate F was obtained by separation refining the obtained residue using silica gel pipe chromatography after obtaining a residue by drying the collected organic layer using magnesium sulfate and an evaporating solvent. $^1$H NMR (CDCl$_3$, 300 MHz)δ(ppm) 8.2(d, 1H), 8.12-8.02(m, 2H), 7.60(d, 1H), 7.54-7.44(m, 2H), 7.43-7.34(m, 1H), 7.28-7.19(m, 1H), 6.91(d, 1H).

Synthesis of Intermediate G

The solution was heated at 170° C. for 8 hours after dissolving 335 mg (2 mmol) of carbazole, 1.2 g (5 mmol) of 1,4-dibromobenzene, 76 mg (0.4 mmol) of CuI, 1.1 g (8 mmol) of K$_2$CO$_3$ and 10 mg (0.04 mmol) of 18-crown-6 into 5 ml of DMPU(1,3-dimethyl-3,4,5,6-tetrahydro-(1H)-pyrimidinone). The solution was washed three times using 10 ml of diethyl ether after cooling the solution to room temperature, filtering the solid materials from the cooled solution, and adding a small quantity of ammonia water to the filtrate. A coarse product was obtained by reduced pressure drying the dried diethyl ether layer after drying the washed diethyl ether layer using MgSO$_4$. 480 mg (a yield of 75%) of solid phase intermediate G was obtained by separation refining the obtained coarse product using silica gel pipe chromatography. $^1$H NMR (CDCl$_3$, 400 MHz)δ(ppm) 8.12(d, 2H), 7.70(d, 2H), 7.3-7.34(m, 6H), 7.30-7.26(m, 2H).

Synthesis of Intermediate H

A reaction solution was prepared by agitating the solution for 2 hours after dissolving 200 mg (0.62 mmol) of intermediate G into 3 ml of THF and adding 0.325 ml (0.806 mmol) of 2.5 mol n-butyllithium dissolved into n-hexane to the dissolved solution dropwise. After putting 0.2 ml (1.86 mmol) of trimethylborate into the reaction solution, the mixed solution was agitated at the same temperature as the reaction solution for 3 hours and agitated at room temperature for 12 hours. The pH adjusted solution was agitated at room temperature for 2 hours after adjusting the pH of the agitated solution to 1 using 12 M hydrochloric acid aqueous solution. The resulting solution was extracted three times using 50 ml of diethyl ether after adjusting the pH of the agitated solution to 14 using a 4 M NaOH aqueous solution. 145 mg (a yield of 81%) of white solid intermediate H was obtained by separation refining the obtained residue using silica gel pipe chromatography after obtaining a residue by drying the collected organic layer using magnesium sulfate and an evaporating solvent.

Synthesis of Compound of Formula 18

A reaction solution was prepared by dissolving 40 mg (0.125 mmol) of intermediate F and 40 mg (0.125 mmol) of intermediate H into 3 ml of THF, adding 3 mg (0.002 mmol) of tetrakisphenylphosphinepalladium to the solution, adding an aqueous solution in which 90 mg (0.6 mmol) of K$_2$CO$_3$ was dissolved into 3 ml of distilled water to the solution, and agitating the resulting solution at 75° C. for 12 hours. The reaction solution was extracted three times using 10 ml of ethylacetate. 50 mg (a yield of 93%) of a compound of Formula 18 was obtained by separation refining the obtained residue using silica gel pipe chromatography after obtaining a residue by drying the collected organic layer using magnesium sulfate and an evaporating solvent. Structure of the obtained compound was confirmed to be $^1$H NMR. $^1$H NMR (CDCl$_3$, 300 MHz)δ(ppm) 8.17(d, 2H), 8.14(dd, 1H), 7.77-7.74(m, 5H), 7.73-7.68(m, 2H), 7.55(d, 2H), 7.46(dt, 2H), 7.37-7.29(m, 5H), 7.28-7.23(m, 1H), 6.83(dt, 1H).

EXAMPLE 2

Figure 9:
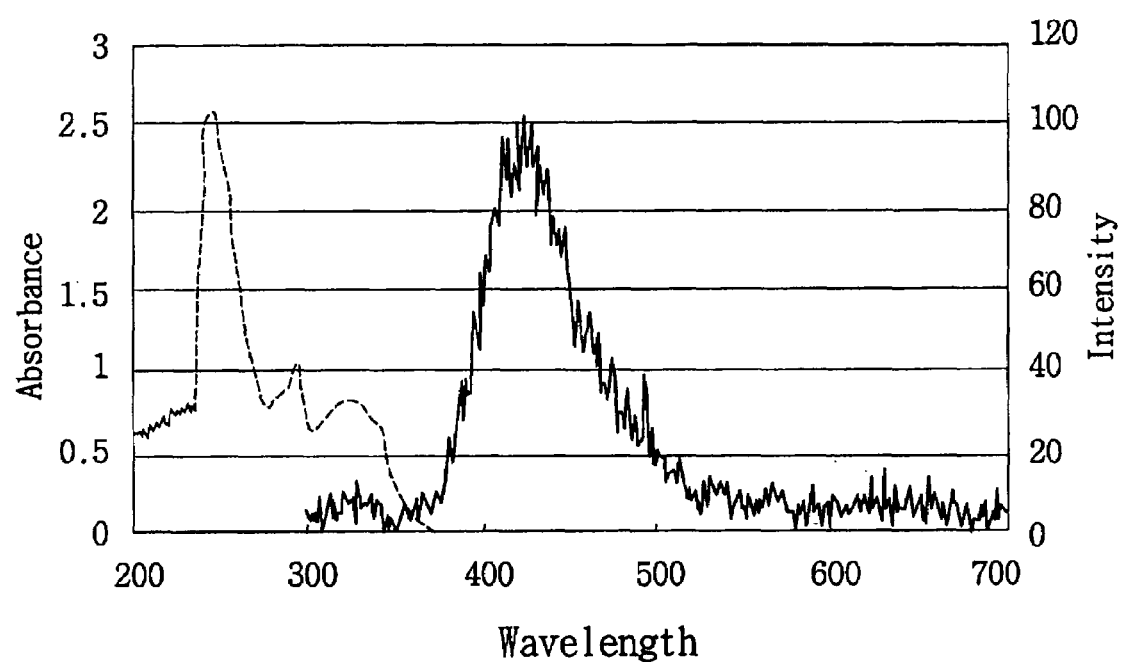
FIG. 9 is an UV absorption spectrum and a PL spectrum of a light-emitting compound of synthesis example 2 of the present invention.

After diluting the compound of Formula 18 to a concentration of 0.2 mM using CHCl$_3$, an UV spectrum of the diluted compound of Formula 18 was obtained, and the maximum absorption wavelength of 324 nm was observed in the UV spectrum. The maximum emission was observed at 429 nm as illustrated in FIG. 9 by measuring PL at 324 nm after diluting the compound of Formula 18 to a concentration of 10 mM using CHCl$_3$, wherein a color purity of CIE(x, y):0.2237, 0.1418 was obtained at NTSC (National Television System Committee) color coordinates, wherein the NTSC is an organization that formulates standards for the current U.S. color television system and most countries of the Americas.

SYNTHESIS EXAMPLE 3 (PREPARATION OF COMPOUND OF FORMULA 19)

A compound of Formula 19 was synthesized according to the reaction path of chemical Reaction Formula 3.

Formula 19

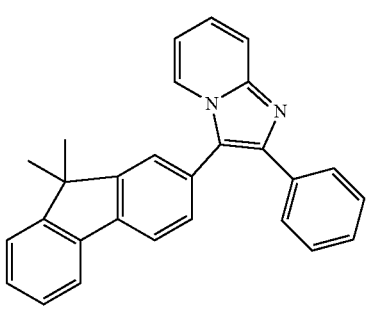

Reaction Formula 3

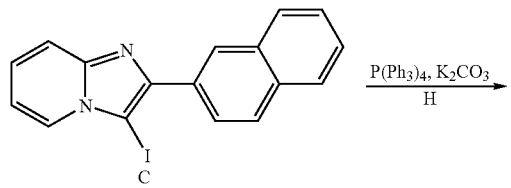

-continued

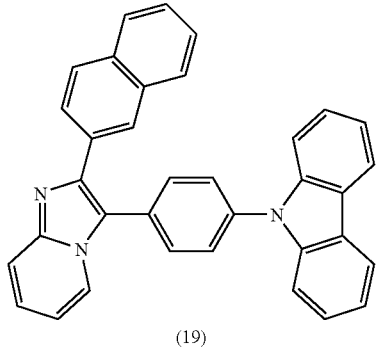

(19)

A reaction solution was prepared by dissolving 32 mg (0.087 mmol) of intermediate C and 25 mg (0.087 mmol) of intermediate H into 3 ml of THF, adding 2 mg (0.002 mmol) of tetrakistriphenylphosphinepalladium to the solution, adding an aqueous solution in which 60 mg (0.43 mmol) of K$_2$CO$_3$ was dissolved into 3 ml of distilled water to the solution and agitating the resulting solution at 75° C. for 12 hours. The reaction solution was extracted three times using 10 ml of ethylacetate. 41 mg (a yield of 97%) of a compound of Formula 19 was obtained by separation refining the obtained residue using silica gel pipe chromatography after obtaining a residue by drying the collected organic layer using magnesium sulfate and an evaporating solvent. The structure of the obtained compound was confirmed to be $^1$H NMR. $^1$H NMR (CDCl$_3$, 300 MHz)δ(ppm) 8.29(s, 1H), 8.21-8.17(m, 3H), 7.85-7.73(m, 9H), 7.56(d, 2H), 7.50-7.46(m, 4H), 7.37-7.25 (m, 3H), 6.86(t, 1H).

EXAMPLE 3

Figure 10:
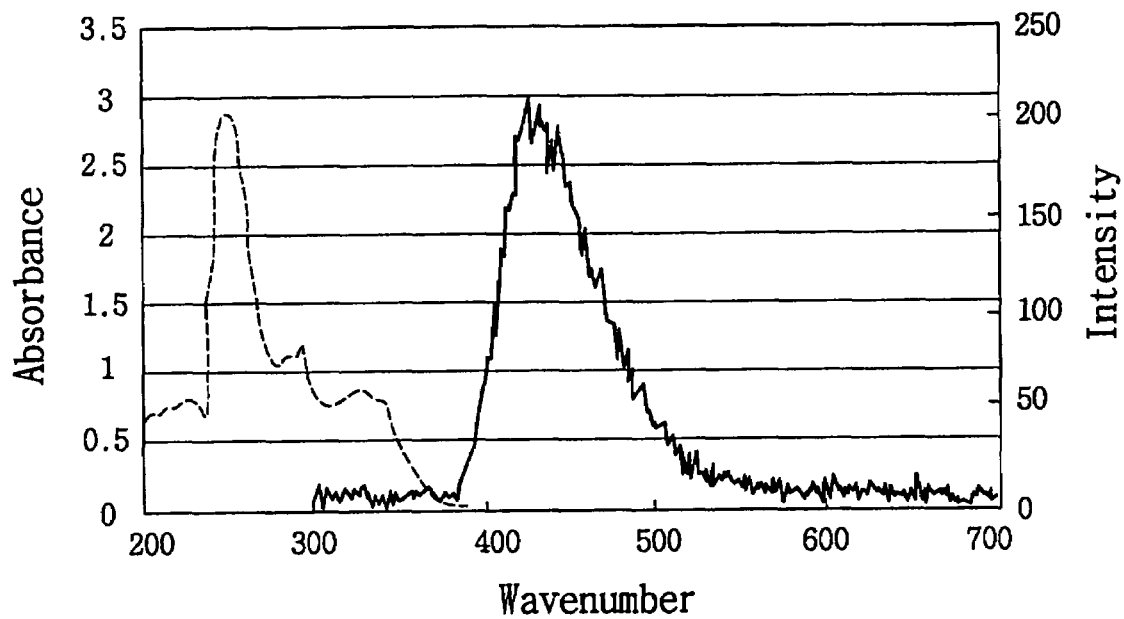
FIG. 10 is an UV absorption spectrum and a PL spectrum of a light-emitting compound of synthesis example 3 of the present invention.

After diluting the compound of Formula 19 to a concentration of 0.2 mM using CHCl$_3$, an UV spectrum of the diluted compound of Formula 19 was obtained, and the maximum absorption wavelength of 327.5 nm was observed in the UV spectrum. The maximum emission was observed at 432 nm, as illustrated in FIG. 10, by measuring PL at 327.5 nm after diluting the compound of Formula 19 to a concentration of 10 mM using CHCl$_3$, wherein a color purity of CIE(x, y):0.1907, 0.1106 was obtained at NTSC color coordinates.

SYNTHESIS EXAMPLE 4 (PREPARATION OF COMPOUND OF FORMULA 20)

A compound of Formula 20 was synthesized according to the reaction path of chemical Reaction Formula 4.

Formula 20

Reaction Formula 4

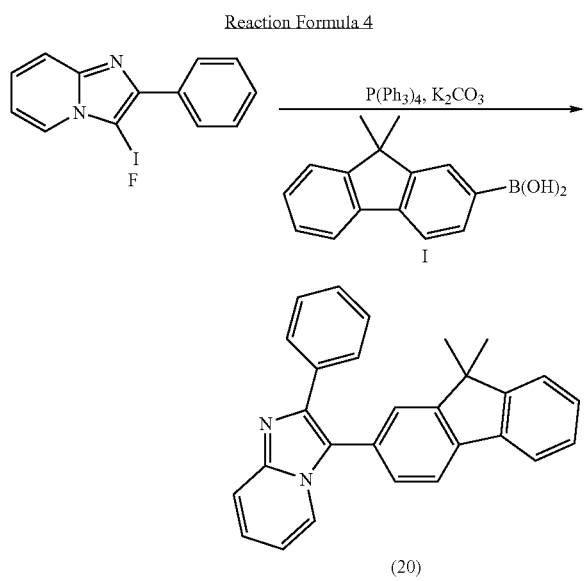

Synthesis of Compound I

A reaction solution was prepared by agitating the solution for 2 hours after dissolving 1.63 g (6 mmol) of 2-bromo-9,9'-dimethylfluorene into 20 ml of THF and adding 3.2 ml (7.8 mmol) of 2.5 mol n-butyllithium dissolved into n-hexane to the dissolved solution dropwise at −78° C. After putting 2 ml (18 mmol) of trimethylborate into the reaction solution, the mixed solution was agitated at the same temperature as the reaction solution for 3 hours and agitated at room temperature for 12 hours. The pH adjusted solution was agitated at room temperature for 2 hours after adjusting the pH of the agitated solution to 1 using 12 M hydrochloric acid aqueous solution. The resulting solution was extracted three times using 50 ml of diethyl ether after adjusting the pH of the agitated solution to 14 using a 4 M NaOH aqueous solution. 1 g (yield of 72%) of white solid intermediate C was obtained by separation refining the obtained residue using silica gel pipe chromatography after obtaining a residue by drying the collected organic layer using magnesium sulfate and an evaporating solvent. $^1$H NMR (CDCl$_3$, 400 MHz)δ(ppm) 8.32(s, 2H), 7.91-7.90(m, 2H), 7.51(s, 1H), 7.39(s, 2H), 1.63(s, 2H).

Preparation of Compound of Formula 20

A reaction solution was prepared by dissolving 40 mg (0.125 mmol) of intermediate F and 30 mg (0.125 mmol) of intermediate I into 3 ml of THF, adding 3 mg (0.002 mmol) of tetrakistriphenylphosphinepalladium to the solution, adding an aqueous solution in which 90 mg (0.6 mmol) of K$_2$CO$_3$ was dissolved into 3 ml of distilled water to the solution and agitating the resulting solution at 75° C. for 12 hours. The reaction solution was extracted three times using 10 ml of ethylacetate. 43 mg (yield of 89%) of compound of Formula 20 was obtained by separation refining the obtained residue using silica gel pipe chromatography after obtaining a residue by drying the collected organic layer using magnesium sulfate and an evaporating solvent. The structure of the obtained compound was confirmed to be $^1$H NMR. $^1$H NMR (CDCl$_3$, 300 MHz)δ(ppm) 8.08(d, 1H), 7.87(d, 1H), 7.80-7.78(m, 1H), 7.73-7.68(m, 3H), 7.49-7.45(m, 3H), 7.40-7.35(m, 2H), 7.27-7.20(m, 4H), 6.76(s, 1H), 1.47(s, 6H).

EXAMPLE 4

Figure 11:
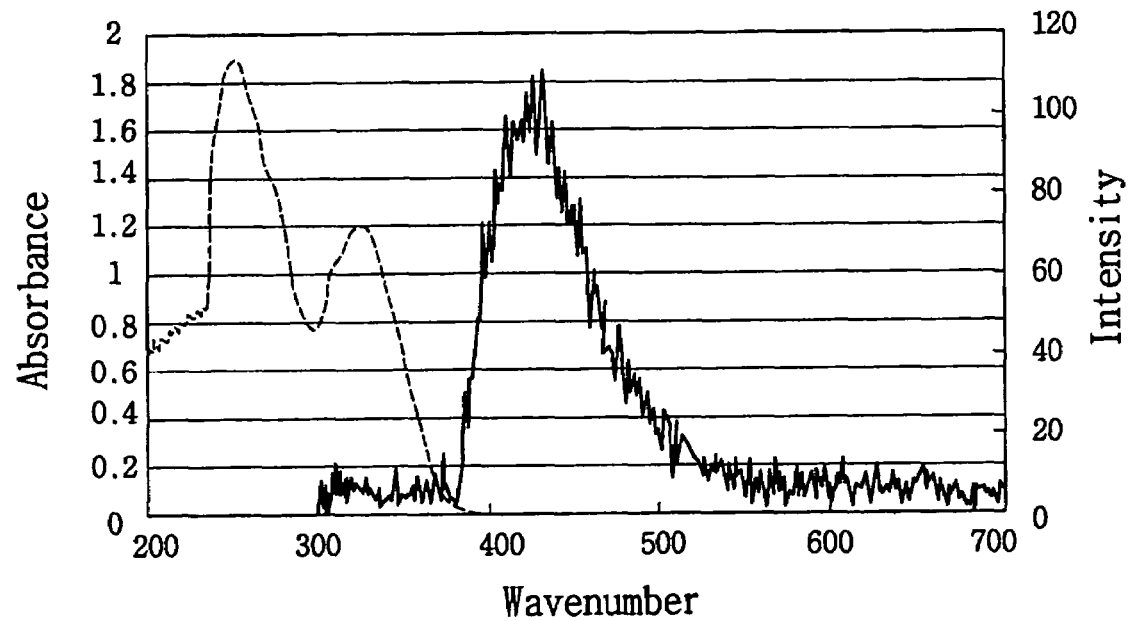
FIG. 11 is an UV absorption spectrum and a PL spectrum of a light-emitting compound of synthesis example 4 of the present invention.

After diluting the compound of Formula 20 to a concentration of 0.2 mM using CHCl$_3$, an UV spectrum of the diluted compound of Formula 20 was obtained, and the maximum absorption wavelength 324 nm was observed in the UV spectrum. The maximum emission was observed at 432 nm, as illustrated in FIG. 11, by measuring PL at 324 nm after diluting compound of Formula 20 to a concentration of 10 mM using CHCl$_3$, wherein a color purity of CIE(x, y):0.219, 0.1372 was obtained at NTSC color coordinates.

SYNTHESIS EXAMPLE 5 (PREPARATION OF COMPOUND OF FORMULA 21)

45 mg (a yield of 98%) of the compound of Formula 21 was obtained by reacting 37 mg (0.1 mmol) of intermediate C with 27 mg (0.1 mmol) of compound I by the same method as synthesis of the compound of Formula 20. The structure of the obtained compound was confirmed to be $^1$H NMR. $^1$H NMR (CDCl$_3$, 400 MHz)δ(ppm) 8.32(s, 1H), 8.12(d, 1H), 7.90(d, 1H), 7.83-7.67(m, 6H), 7.55(s, 1H), 7.52-7.46(m, 2H), 7.44-7.35(m, 4H), 7.27-7.23(m, 1H), 6.78(t, 1H), 1.47(s, 6H).

Formula 21

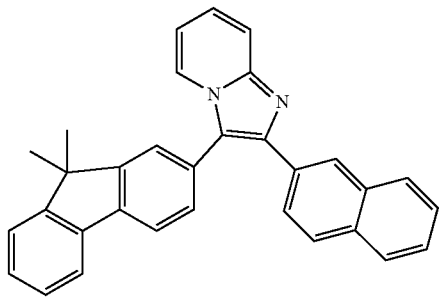

EXAMPLE 5

Figure 12:
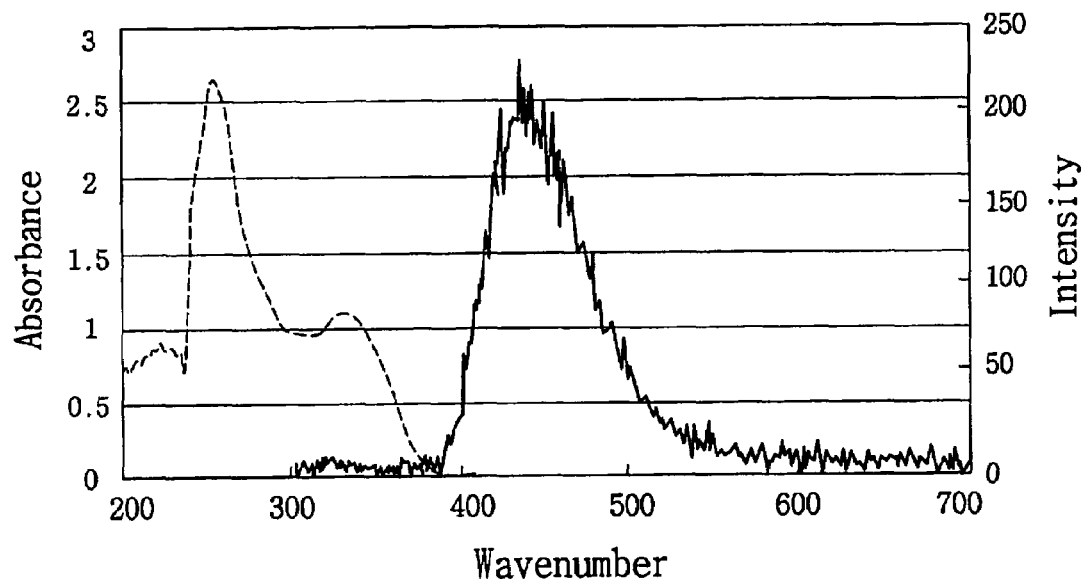
FIG. 12 is an UV absorption spectrum and a PL spectrum of a light-emitting compound of synthesis example 5 of the present invention.

After diluting the compound of Formula 21 to a concentration of 0.2 mM using CHCl$_3$, an UV spectrum of the diluted compound of Formula 21 was obtained, and the maximum absorption wavelength 330 nm was observed in the UV spectrum. The maximum emission was observed at 437 nm, as illustrated in FIG. 12, by measuring PL at 330 nm after diluting compound of Formula 21 to a concentration of 10 mM using CHCl$_3$, wherein a color purity of CIE(x, y):0.1921, 0.1238 was obtained at NTSC color coordinates.

SYNTHESIS EXAMPLE 6 (PREPARATION OF COMPOUND OF FORMULA 22)

A compound of Formula 22 was synthesized according to the reaction path of chemical Reaction Formula 5.

Formula 22

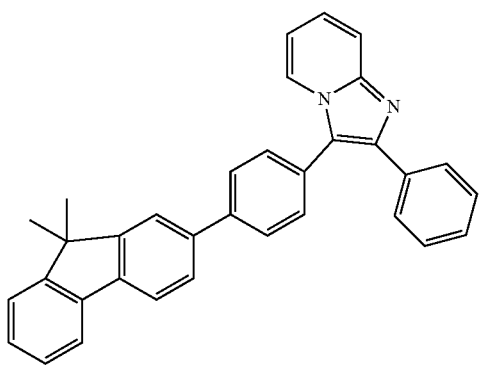

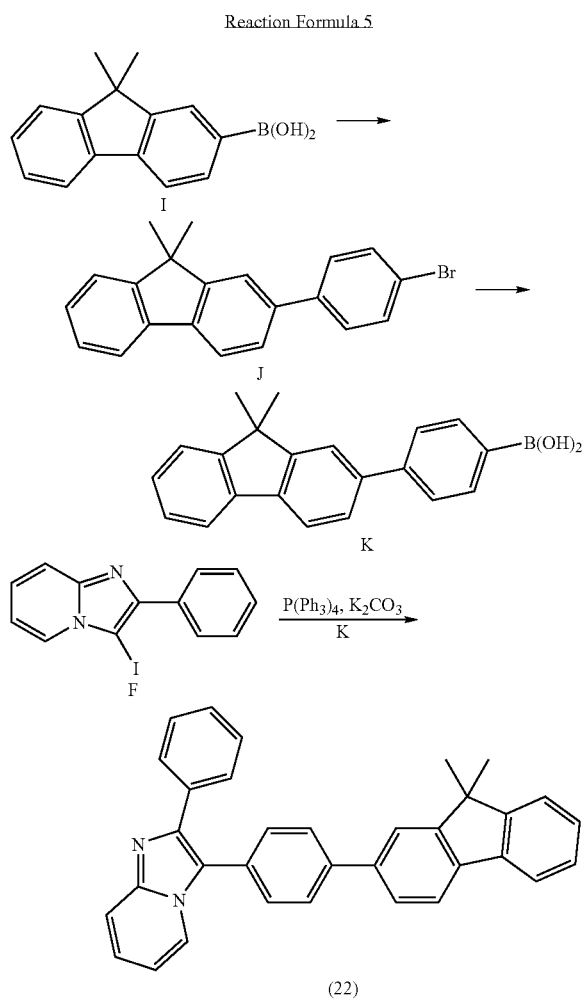

Synthesis of Intermediate J

A reaction solution was prepared by dissolving 100 mg (0.42 mmol) of compound I and 250 mg (1.05 mmol) of 1,4-dibromobenzene into 5 ml of THF, adding 10 mg (0.008 mmol) of tetrakistriphenylphosphinepalladium to the solution, adding an aqueous solution in which 580 mg (4.2 mmol) of $K_2CO_3$ was dissolved into 5 ml of distilled water to the solution, and agitating the resulting solution at 75° C. for 12 hours. The reaction solution was extracted three times using 10 ml of ethylacetate. 100 mg (a yield of 67%) of intermediate J was obtained by separation refining the obtained residue using silica gel pipe chromatography after obtaining a residue by drying the collected organic layer using magnesium sulfate and an evaporating solvent. The structure of the obtained intermediate J was confirmed to be $^1H$ NMR. $^1H$ NMR ($CDCl_3$, 400 MHz)δ(ppm) 7.78(s, 1H), 7.75-7.73(m, 1H), 7.60-7.55(m, 3H), 7.54-7.50(m, 3H), 7.46-7.43(m, 1H), 7.37-7.31(m, 2H), 1.53(s, 6H).

Synthesis of Intermediate K

A reaction solution was prepared by agitating the solution for 2 hours after dissolving 560 mg (1.6 mmol) of intermediate J into 10 ml of THF and adding 0.85 ml (2.08 mmol) of 2.5 mol n-butyllithium dissolved into n-hexane to the dissolved solution dropwise at −78° C. After putting 0.45 ml (4 mmol) of trimethylborate into the reaction solution, the mixed solution was agitated at the same temperature as the reaction solution for 3 hours and agitated at room temperature for 12 hours. The pH adjusted solution was agitated at room temperature for 2 hours after adjusting the pH of the agitated solution to 1 using 12 M hydrochloric acid aqueous solution. The resulting solution was extracted three times using 50 ml of diethyl ether after adjusting the pH of the agitated solution to 14 using a 4 M NaOH aqueous solution. 390 mg (a yield of 77%) of white solid intermediate K was obtained by separation refining the obtained residue using silica gel pipe chromatography after obtaining a residue by drying the collected organic layer using magnesium sulfate and an evaporating solvent.

Synthesis of Compound of Formula 22

976 mg (a yield of 89%) of the compound of Formula 22 was obtained by reacting 759 mg (2.37 mmol) of intermediate F with 745 mg (2.37 mmol) of intermediate K by the same method as in the synthesis of the compound of Formula 20. A white solid was obtained by sublimation refining the obtained compound at 260° C. under the nitrogen pressure of 1 torr using a sublimation refining apparatus. The structure of the obtained compound was confirmed to be $^1H$ NMR. $^1H$ NMR ($CDCl_3$, 400 MHz)δ(ppm) 8.05(d, 1H), 7.84(dd, 3H), 7.76-7.65(m, 6H), 7.55(d, 2H), 7.46(dd, 1H), 7.39-7.18(m, 6H), 6.76(dt, 1H), 134.1, 131.0, 128.5, 128.3, 128.2, 128.1, 127.5, 127.4, 127.1, 126.1, 124.7, 123.3, 122.6, 121.2, 120.8, 120.4, 120.1, 117.6, 112.3, 46.9, 27.2.

EXAMPLE 6

Figure 13:
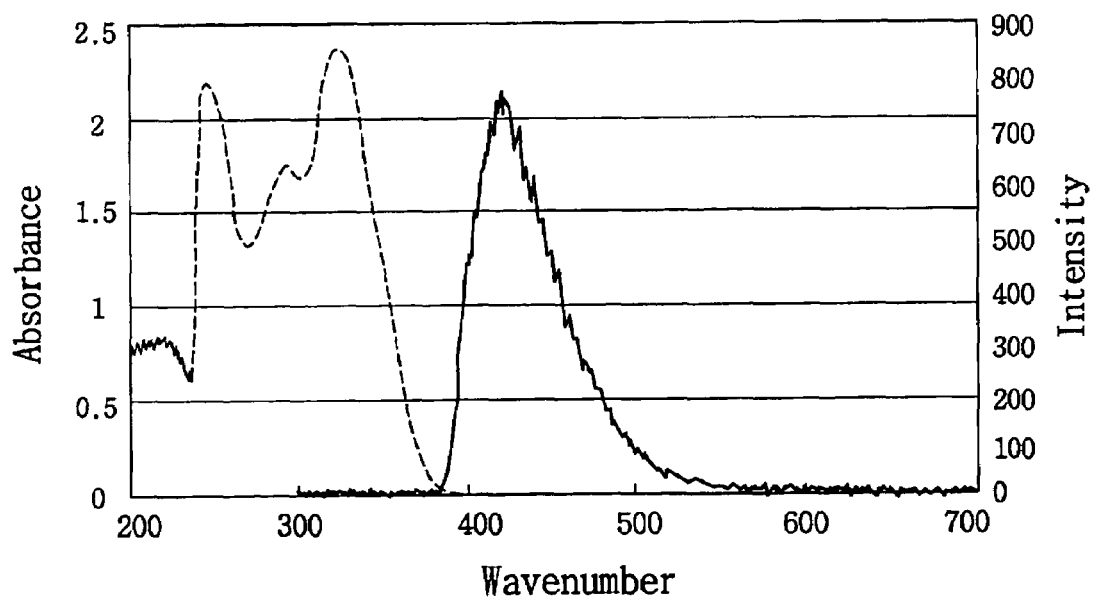
FIG. 13 is an UV absorption spectrum and a PL spectrum of a light-emitting compound of synthesis example 6 of the present invention.
Figure 14:
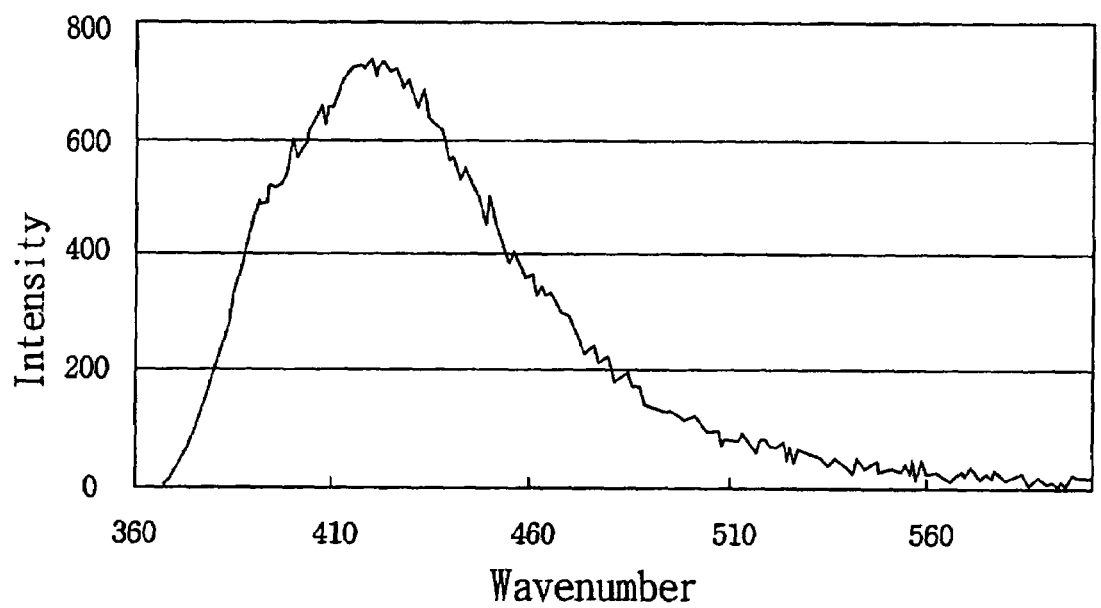
FIG. 14 is a PL spectrum of a mixture of polymethylmethacrylate and the light-emitting compound of synthesis example 6 of the present invention.
Figure 15:
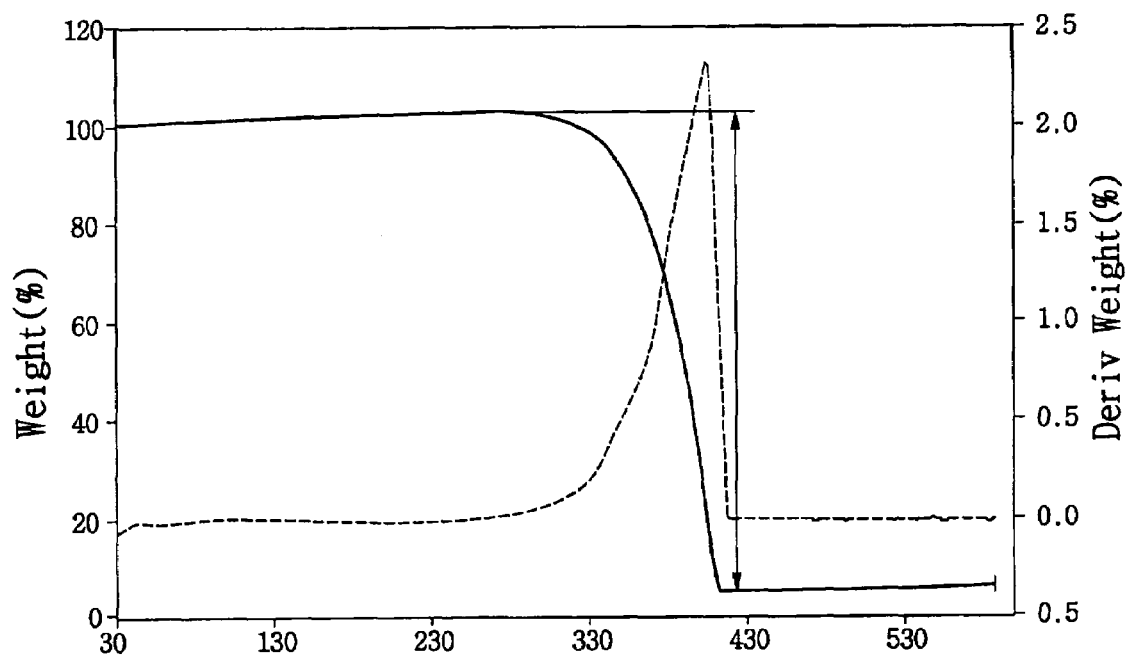
FIG. 15 is a TGA (Thermo Gravimetric Analysis) graph of the light-emitting compound of synthesis example 6 of the present invention.
Figure 16:
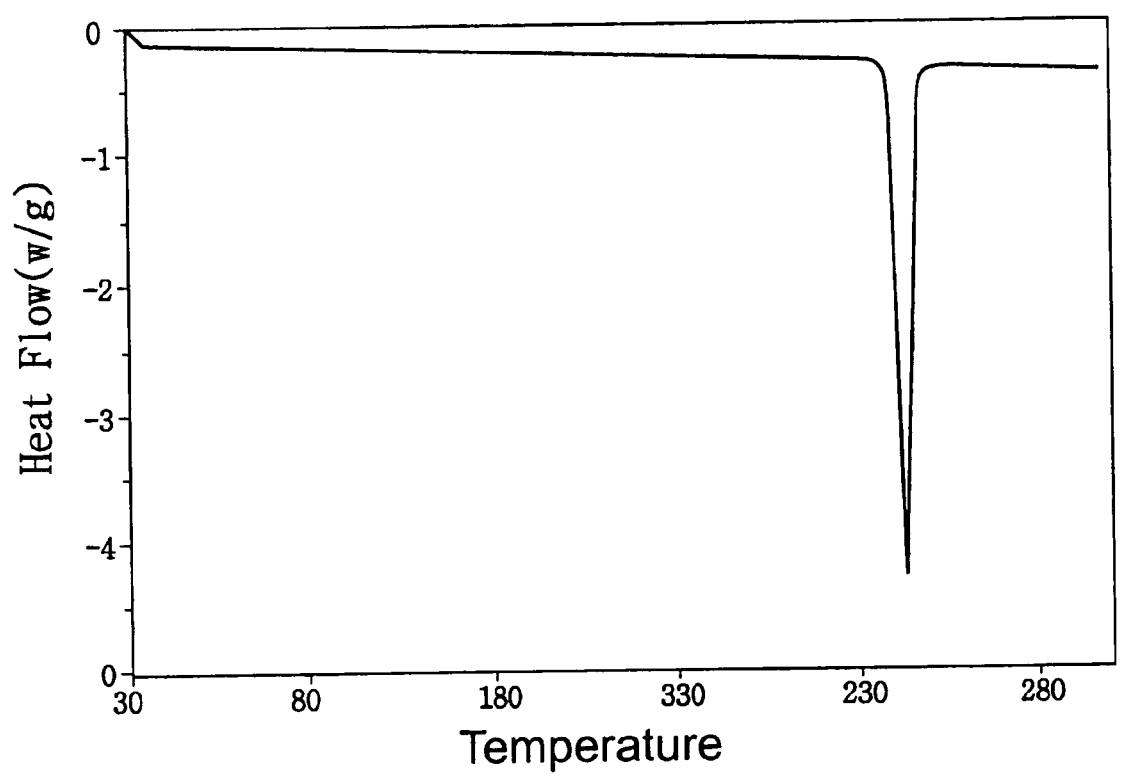
FIG. 16 is a DSC (Differential Scanning Calorimetry) graph of the light-emitting compound of synthesis example 6 of the present invention.
Figure 17:
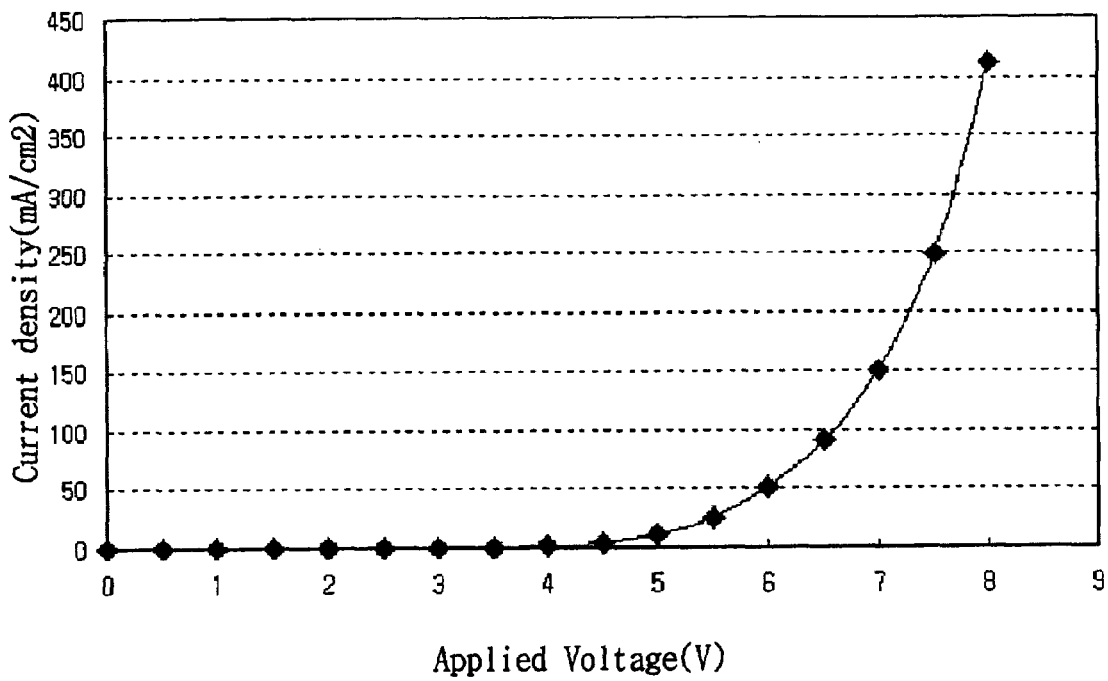
FIG. 17 is a current density-voltage graph obtained by measuring the current density and voltage of the fabricated organic electroluminescent device after fabricating an organic electroluminescent device using the light-emitting compound of synthesis example 6 of the present invention.
Figure 18:
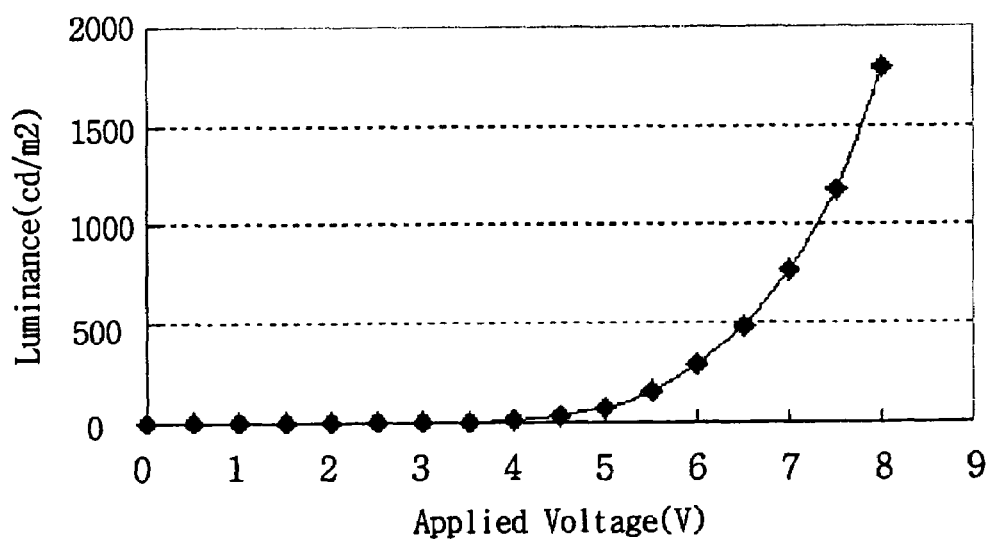
FIG. 18 is a luminance-voltage graph obtained by measuring the luminance and voltage of the fabricated organic electroluminescent device after fabricating an organic electroluminescent device using the light-emitting compound of synthesis example 6 of the present invention.
Figure 19:
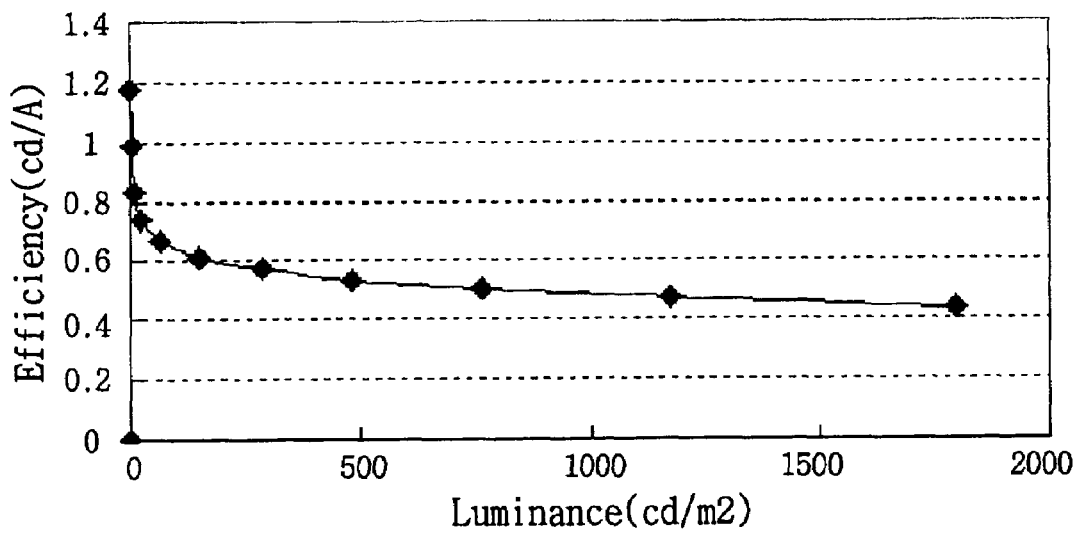
FIG. 19 is an efficiency-luminance graph obtained by measuring the efficiency and luminance of the fabricated organic electroluminescent device after fabricating an organic electroluminescent device using the light-emitting compound of synthesis example 6 of the present invention.
Figure 20:
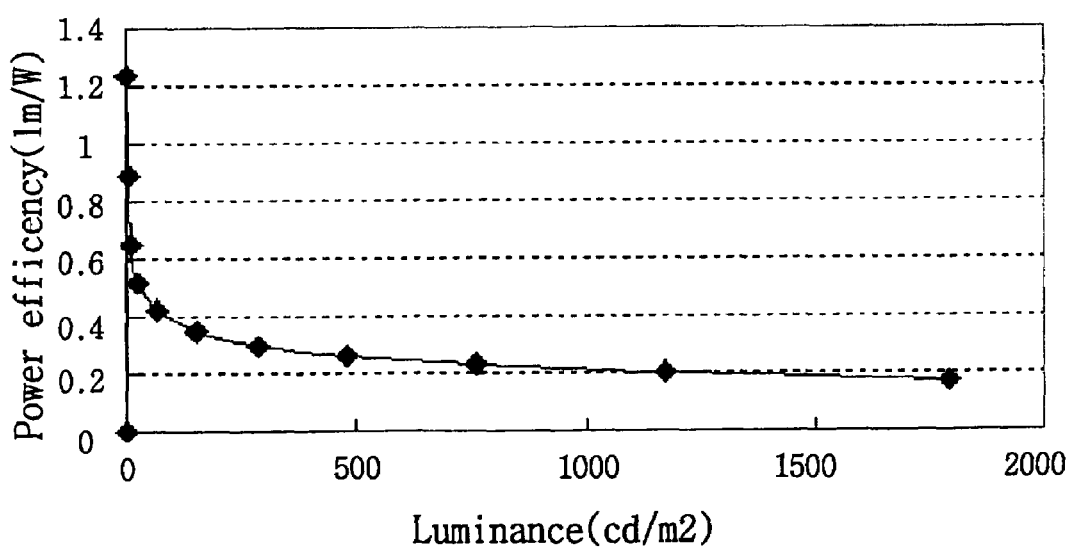
FIG. 20 is a power supply efficiency-luminance graph obtained by measuring the power supply efficiency and luminance of the fabricated organic electroluminescent device after fabricating an organic electroluminescent device using the light-emitting compound of synthesis example 6 of the present invention.
Figure 21:
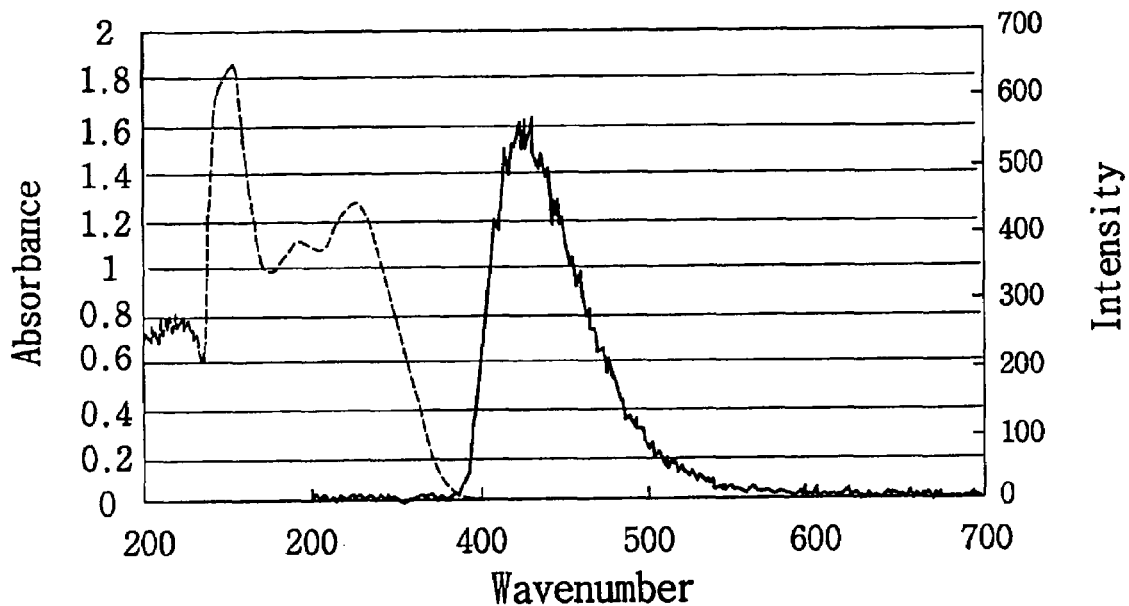
FIG. 21 is an UV absorption spectrum and a PL spectrum of a light-emitting compound of synthesis example 7 of the present invention.

After diluting the compound of Formula 22 to a concentration of 0.2 mM using $CHCl_3$, an UV spectrum of the diluted compound of Formula 22 was obtained, and the maximum absorption wavelength 322.5 nm was observed in the UV spectrum. The maximum emission was observed at 420 nm, as illustrated in FIG. 13, by measuring PL at 322.5 nm after diluting compound of Formula 22 to a concentration of 10 mM using $CHCl_3$, wherein a color purity of CIE(x, y):0.1719, 0.0698 was obtained at NTSC color coordinates. Furthermore, the maximum emission was observed at 418 nm, as illustrated in FIG. 14, by measuring PL of the thin film after dissolving a mixture of the compound of Formula 21 and polymethylmethacrylate (PMMA) mixed in a ratio of 15:1 into chloroform and forming a thin film by spin coating the solution on a glass substrate (50 mm×50 mm×1.0 mm), wherein a color purity of CIE(x, y):0.1641, 0.0882 was obtained at NTSC color coordinates. Furthermore, Td 343° C., Tg 101° C. and Tm 239° C. were obtained, as illustrated in FIG. 15 and FIG. 16, through thermal analysis ($N_2$ atmosphere, temperature section: room temperature to 600° C. (10° C./min)-TGA, DSC from ordinary temperature to 400° C., Pan Type: Pt Pan in disposable Al Pan (TGA) and disposable Al pan (DSC) using TGA (Thermo Gravimetric Analysis) and DSC (Differential Scanning Calorimetry) for the compound of Formula 22. A HOMO (Highest Occupied Molecular Orbital) energy level of 5.79 eV and a LUMO (Lowest Unoccupied Molecular Orbital) energy level of 2.64 eV were obtained through the UV absorption spectrum and by using a Photoelectron Spectrometer, Model AC-2 Surface Analyzer, to measure an ionization energy.

EXAMPLE 7

A compound of Formula 22 was applied to an organic electroluminescent device. ITO having $15/cm^2$ (1200 Å) manufactured by CORNING CORPORATION was used as the anode. A glass substrate was cut to a size of 50 mm×50 mm×0.7 mm, and the cut glass substrate was cleaned by ultrasonic waves respectively in isopropyl alcohol and pure water for 5 minutes and cleaned by UV ozone for 30 minutes before the cleaned glass substrate was used. A hole injection layer was formed to a thickness of 600 Å by vacuum depositing IDE406 on an upper part of the substrate. Subsequently, a hole transport layer was formed by vacuum depositing 4,4'-bis biphenyl (hereinafter referred to as "NPB") to a thickness of 300 Å on an upper part of the hole injection layer. An emitting layer was formed to a thickness of 200 Å by vacuum depositing a compound of Formula 2 on an upper part of the hole transport layer after forming the hole transport layer. After forming the emitting layer, an electron transport layer having a thickness of 250 Å was formed by vacuum depositing $Alq_3$ on an upper part of the emitting layer. An organic electroluminescent device was fabricated, as illustrated in FIG. 1, by sequentially vacuum depositing LiF having a thickness of 10 Å as an electron injection layer and Al having a thickness of 3,000 Å as a cathode electrode on an upper part of the electron transport layer, thus forming a LiF/Al electrode. Referring to FIG. 17 to FIG. 20, the device had an emission luminance of 286 $cd/m^2$, an emission efficiency of 0.57 cd/A and color coordinates of 0.1532 and 0.1146 at a DC voltage of 6 V, so that a blue emitting compound having an effective purity was obtained.

SYNTHESIS EXAMPLE 7 (PREPARATION OF COMPOUND OF FORMULA 23)

78 mg (a yield of 84%) of the compound of Formula 23 was obtained by reacting 67.5 mg (0.18 mmol) of intermediate C with 63 mg (0.18 mmol) of intermediate K by the same method as the synthesis of the compound of Formula 20. The structure of the obtained compound was confirmed to be $^1H$ NMR. $^1H$ NMR ($CDCl_3$, 400 MHz)δ(ppm) 8.35(s, 1H), 8.10 (d, 1H), 7.86-7.70(m, 10H), 7.68(dd, 1H), 7.58(dd, 2H), 7.49-7.41(m, 3H), 7.38-7.35(m, 2H), 7.27-7.23(m, 1H), 6.79(dt, 1H), 1.57(s, 6H).

EXAMPLE 8

After diluting the compound of Formula 23 to a concentration of 0.2 mM using $CHCl_3$, an UV spectrum of the diluted compound of Formula 23 was obtained, and the maximum absorption wavelength 325 nm was observed in the UV spectrum. The maximum emission was observed at 427 nm, as illustrated in FIG. 2, by measuring PL at 325 nm after diluting compound of Formula 23 to a concentration of 10 mM using $CHCl_3$, wherein a color purity of CIE(x, y):0.1728, 0.0807 was obtained at NTSC color coordinates.

SYNTHESIS EXAMPLE 8 (PREPARATION OF COMPOUND OF FORMULA 25)

A compound of Formula 25 was synthesized according to the reaction path of chemical Reaction Formula 6.

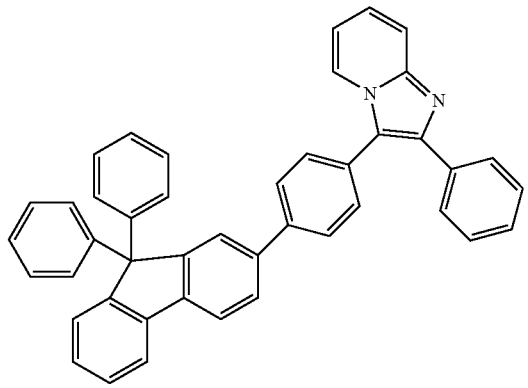

Formula 25

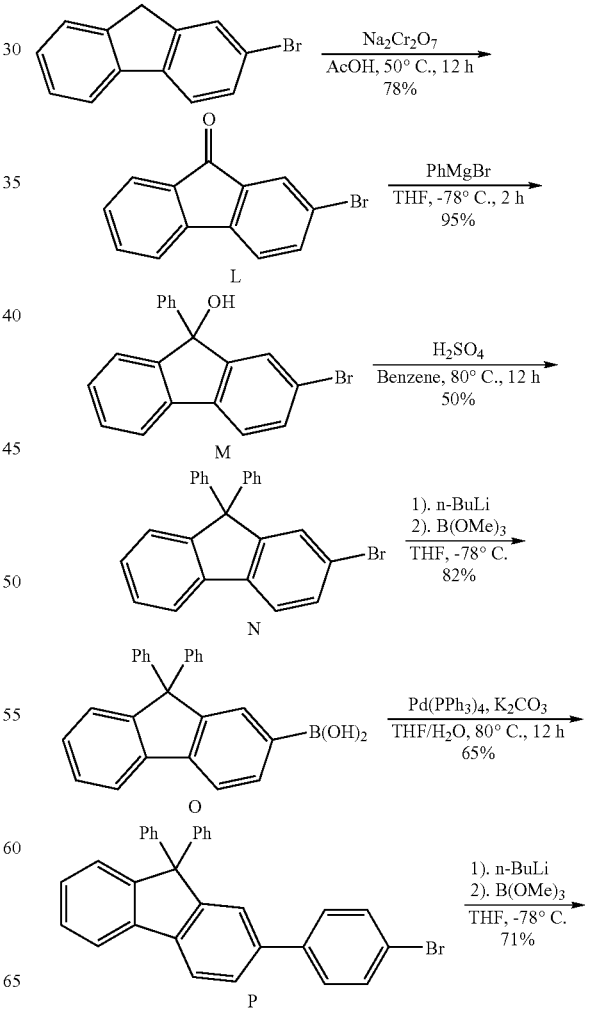

Reaction Formula 6

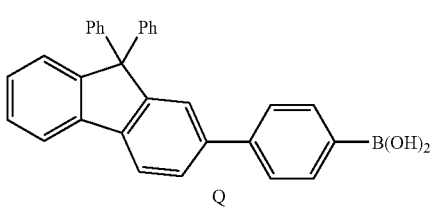

Q

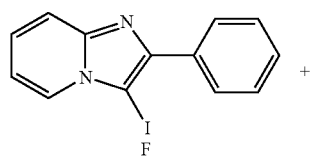

+

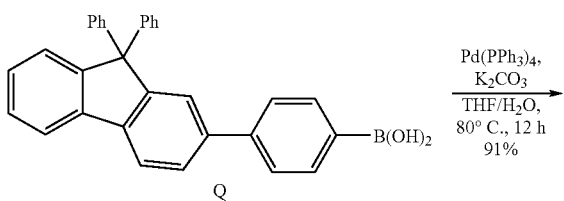

Q

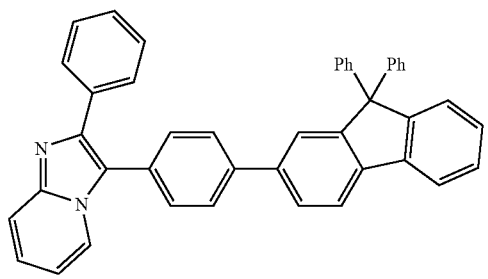

(25)

Synthesis of Intermediate L 60 g (200 mmol) of sodium dichromate was slowly added to the mixture at 0° C. after dissolving 13 g (53 mmol) of 2-bromofluorene into 60 ml of acetic acid. After 12 hours, 200 ml of distilled water was added to the mixture, and the mixed solution was sufficiently agitated so that the distilled water is effectively mixed with the mixture. A produced yellow solid was filtered from the solution, and the filtered yellow solid was dried to obtain 10 g (a yield of 78%) of intermediate L.

Synthesis of Intermediate M 38 ml (38 mmol) of 1 M phenyl magnesium bromide was slowly added to the mixture at −78° C. after dissolving 8 g (31.6 mmol) of intermediate L into 60 ml of THF. After 2 hours, the mixture was agitated for 5 hours while maintaining temperature of the mixture at room temperature. After diluting the agitated mixture using 50 ml of ammonium chloride aqueous solution, the diluted mixture was extracted three times using 40 ml of ethylacetate. 10 g (a yield of 95%) of intermediate M was obtained by separation refining the obtained residue using silica gel pipe chromatography after obtaining a residue by drying the collected organic layer using magnesium sulfate and an evaporating solvent. The structure of the obtained intermediate M was confirmed to be $^1$H NMR 7.39-7.33(m, 3H), 7.30-7.23(m, 5H), 2.46(s, 1H).

Synthesis of Intermediate N

After dissolving 10 g (30 mmol) of intermediate M into 60 ml of benzene, a solution in which 2.4 ml (45 mmol) of concentrated sulfuric acid was diluted by a small quantity of benzene was added to the mixture. 1 N NaOH was added to remaining filtrate by evaporating benzene from the agitated solution after agitating the mixture at 80° C. for 5 hours. After adjusting the pH of the 1 N NaOH added filtrate to 7, the pH adjusted solution was extracted for three times using 40 ml of ethylacetate. 6 g (a yield of 50%) of intermediate M was obtained by separation refining the obtained residue using silica gel pipe chromatography after obtaining a residue by drying the collected organic layer using magnesium sulfate and an evaporating solvent.

Synthesis of Intermediate O

A reaction solution was prepared by agitating the solution for 2 hours after dissolving 460 mg (1.16 mmol) of intermediate N into 5 ml of THF and adding 0.61 ml (1.5 mmol) of 2.5 mol n-butyllithium dissolved into n-hexane to the dissolved solution dropwise at −78° C. After putting 0.33 ml (2.9 mmol) of trimethylborate into the reaction solution, the mixed solution was agitated at the same temperature as the reaction solution for 3 hours and agitated at room temperature for 12 hours. The pH adjusted solution was agitated at room temperature for 2 hours after adjusting the pH of the agitated solution to 1 using 12 M hydrochloric acid aqueous solution. The resulting solution was extracted three times using 10 ml of diethyl ether after adjusting the pH of the agitated solution to 14 using a 4 M NaOH aqueous solution. 345 mg (a yield of 82%) of white solid intermediate O was obtained by separation refining the obtained residue using silica gel pipe chromatography after obtaining a residue by drying the collected organic layer using magnesium sulfate and an evaporating solvent.

Synthesis of Intermediate P

A reaction solution was prepared by dissolving 344 mg (0.95 mmol) of Intermediate O and 560 mg (2.37 mmol) of 1,4-dibromobenzene into 10 ml of THF, adding 22 mg (0.02 mmol) of tetrakistriphenylphosphinepalladium to the solution, adding an aqueous solution in which 660 mg (4.8 mmol) of K$_2$CO$_3$ was dissolved into 8 ml of distilled water to the solution and agitating the resulting solution at 75° C. for 12 hours. The reaction solution was extracted three times using 15 ml of ethylacetate. 280 mg (a yield of 65%) of intermediate P was obtained by separation refining the obtained residue using silica gel pipe chromatography after obtaining a residue by drying the collected organic layer using magnesium sulfate and an evaporating solvent. The structure of the obtained intermediate P was confirmed to be $^1$H NMR (CDCl$_3$, 400 MHz)δ(ppm) 7.79(dd, 1H), 7.77(dd, 1H), 7.57(d, 1H), 7.54 (dd, 1H), 7.49(dd, 2H), 7.42-7.37(m, 3H), 7.35(dd, 1H), 7.27 (dt, 1H), 7.25-7.19(m, 10H); 13C NMR (CdCl3, 100 MHz)δ (ppm) 152.0, 151.8, 145.8, 140.2, 139.8, 139.6, 139.5, 131.8, 128.7, 128.3, 128.1, 127.9, 127.6, 126.7, 126.5, 124.7, 120.5, 120.3, 65.6.

Synthesis of Intermediate Q

A reaction solution was prepared by agitating the solution for 2 hours after dissolving 286 mg (0.6 mmol) of intermediate P into 5 ml of THF and adding 0.32 ml (0.78 mmol) of 2.5 mol n-butyllithium dissolved into n-hexane to the dissolved solution dropwise at −78° C. After putting 0.2 ml (1.5 mmol)

of trimethylborate into the reaction solution, the mixed solution was agitated at the same temperature as the reaction solution for 3 hours and agitated at room temperature for 12 hours. The pH adjusted solution was agitated at room temperature for 2 hours after adjusting the pH of the agitated solution to 1 using 12 M hydrochloric acid aqueous solution. The resulting solution was extracted three times using 10 ml of diethyl ether after adjusting the pH of the agitated solution to 14 using a 4 M NaOH aqueous solution. 187 mg (a yield of 71%) of white solid intermediate Q was obtained by separation refining the obtained residue using silica gel pipe chromatography after obtaining a residue by drying the collected organic layer using magnesium sulfate and an evaporating solvent.

Synthesis of Compound of Formula 25

121 mg (yield of 91%) of compound of Formula 25 was obtained by reacting 73 mg (0.23 mmol) of intermediate F with 100 mg (0.23 mmol) of intermediate Q by the same method as in the synthesis of the compound of Formula 20. The structure of the obtained compound was confirmed to be $^1$H NMR (CDCl$_3$, 400 MHz)δ(ppm) 7.99(d, 1H), 7.85(d, 1H), 7.80(d, 1H), 7.71-7.76(m, 7H), 7.47(dd, 2H), 7.42(d, 1H), 7.38(dt, 1H), 7.31-7.16(15H), 6.72(dt, 1H); $^{13}$C NMR (CDCl$_3$, 100 MHz)δ(ppm) 152.1, 151.5, 145.8, 144.9, 142.6, 141.4, 139.9, 139.7, 139.6, 134.1, 130.9, 128.3, 128.2, 128.1, 127.5, 126.7, 126.6, 124.7, 124.6, 123.3, 120.7, 120.6, 120.3, 117.6, 112.3, 65.6.

EXAMPLE 9

Figure 22:
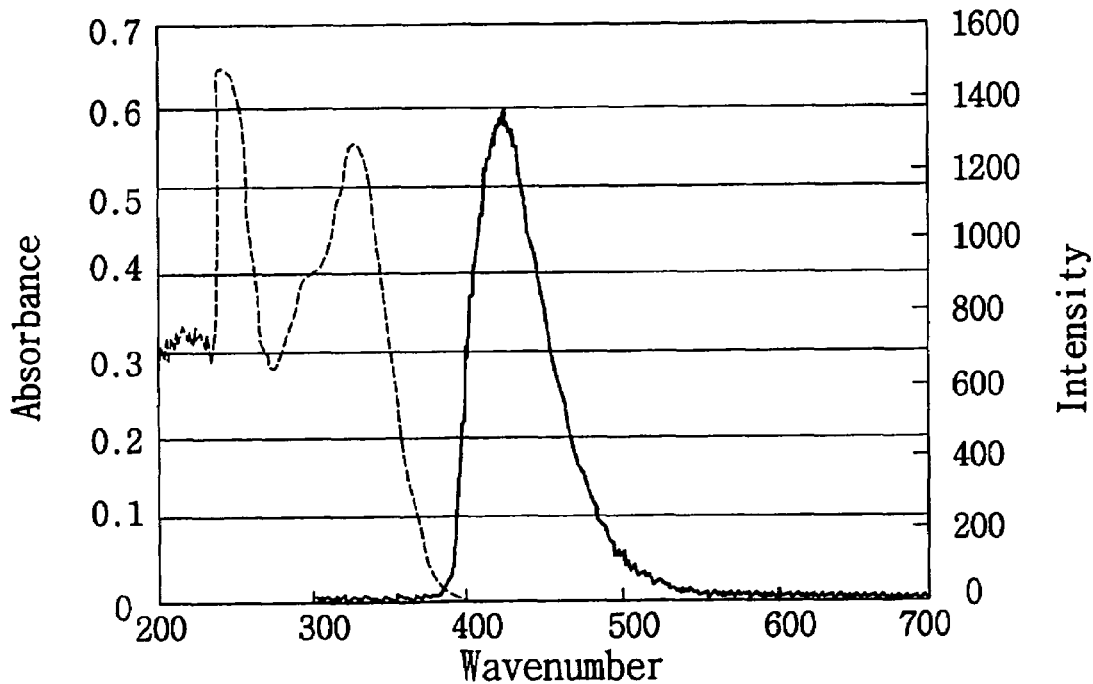
FIG. 22 is an UV absorption spectrum and a PL spectrum of a light-emitting compound of synthesis example 8 of the present invention.
Figure 23:
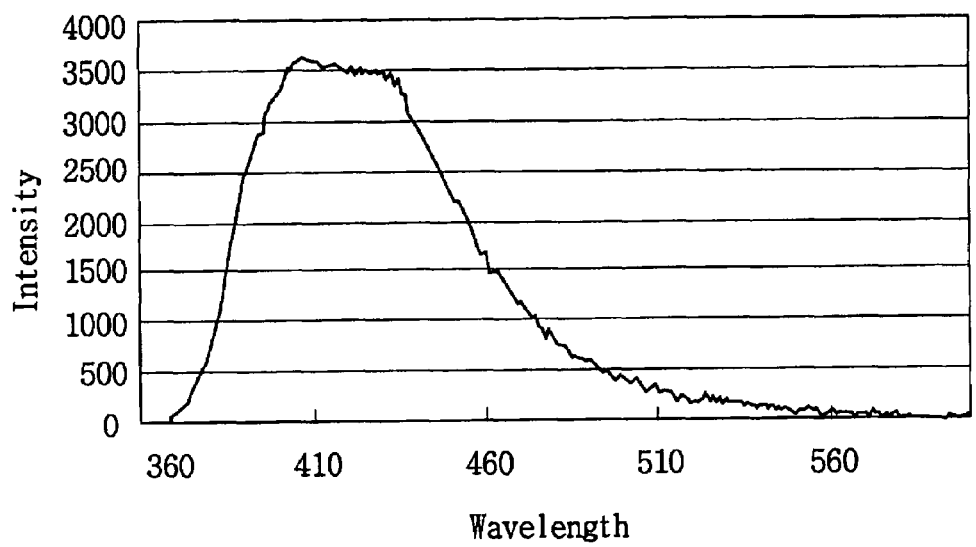
FIG. 23 is a PL spectrum of a mixture of polymethylmethacrylate and the light-emitting compound of synthesis example 8 of the present invention.

After diluting the compound of Formula 25 to a concentration of 0.2 mM using CHCl$_3$, an UV spectrum of the diluted compound of Formula 25 was obtained, and the maximum absorption wavelength 327.5 nm was observed in the UV spectrum. The maximum emission was observed at 424 nm, as illustrated in FIG. 22, by measuring PL at 327.5 nm after diluting compound of Formula 25 to a concentration of 10 mM using CHCl$_3$, wherein a color purity of CIE(x, y):0.1685, 0.0573 was obtained at NTSC color coordinates. Furthermore, the maximum emission was observed at 407 nm, as illustrated in FIG. 23, by measuring PL of the thin film after dissolving a mixture of compound of Formula 25 and polymethylmethacrylate (PMMA) mixed in a ratio of 15:1 into chloroform and forming a thin film by spin coating the solution on a glass substrate (50 mm×50 mm×1.0 mm), wherein a color purity of CIE(x, y):0.1575, 0.0563 was obtained at NTSC color coordinates. A HOMO (Highest Occupied Molecular Orbital) energy level of 5.89 eV and a LUMO (Lowest Unoccupied Molecular Orbital) energy level of 2.77 eV were obtained through an UV absorption spectrum and by using a Photoelectron Spectrometer, Model AC-2 Surface Analyzer, to measure an ionization energy.

EXAMPLES 10 AND 11, COMPARATIVE EXAMPLE

Figure 24:
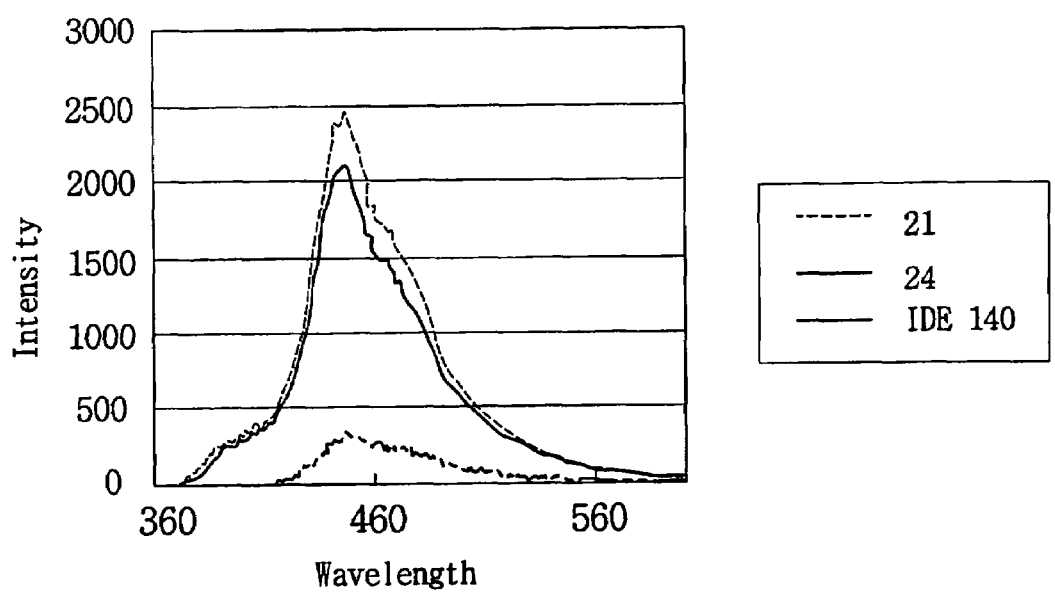
FIG. 24 is a PL spectrum of examples 10 and 11 and the comparative example.

In Examples 10 and 11, PL of the thin film was measured after forming a thin film by adding 5 wt. % of IDE 105, i.e., a blue fluorescent dopant, purchasable from IDEMITSU CORPORATION, used as a dopant to compounds of Formula 22 and 25 used as a host. In Comparative Example 1, the measured PL of the thin film using the compounds of Formula 22 and 25 was compared to the PL of a thin film formed by using IDE 140, i.e., a blue fluorescent host, purchasable from IDEMITSU CORPORATION, under the same conditions as in Examples 10 and 11, as illustrated in FIG. 24, wherein it may be seen that the compounds of Formula 22 and 25 shown a significantly higher intensity at the maximum emission wavelength 444 nm compared to the intensity at the maximum emission wavelength 444 nm using IDE 140.

As described in the above, the present invention provides a light-emitting compound of an organic electroluminescent device having an effective luminance, an efficient driving voltage and an effective color purity, and an organic electroluminescent device using the light-emitting compound by providing an effective light-emitting compound having an imidazole-pyrridine frame.

Although a few embodiments of the present invention have been shown and described, it would be appreciated by those skilled in the art that changes may be made in this embodiment without departing from the principles and spirit of the invention, the scope of which is defined in the claims and their equivalents.

What is claimed is:

1. An emitting compound comprising an imidazo-pyridine frame represented as in the following Formula 1:

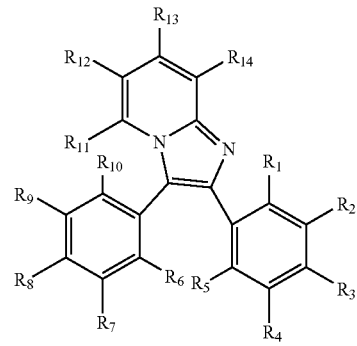

Formula 1 wherein, $R_1$ to $R_{14}$, each of which is independent, are each one functional group selected from the group consisting of a hydrogen atom, a halogen atom, a substituted or a non-substituted alkyl group having 1 to 30 carbon atoms, a substituted or a non-substituted alkoxy group having 1 to 30 carbon atoms, a substituted or a non-substituted aryl group having 6 to 30 carbon atoms, a substituted or a non-substituted aryloxy group having 6 to 30 carbon atoms, a substituted or a non-substituted heterocyclic group having 6 to 30 carbon atoms, a substituted or a non-substituted condensation polycyclic group having 6 to 30 carbon atoms, a substituted or a non-substituted heterocyclic group having 5 to 30 carbon atoms, an amino group, an arylamino group having 6 to 30 carbon atoms, a cyano group, a nitro group, a hydroxy group, an aryl sulfone group having 6 to 30 carbon atoms, and a group that is bonded with an adjacent group of $R_1$ to $R_{14}$ to form a saturated or a nonsaturated carbon ring, and wherein the case of $R_1$ to $R_{10}$ all being hydrogens, the case of any one of $R_1$ to $R_{14}$ being methyl, ethyl, OCH$_3$ or imidazopyridine and the case of $R_3$ being an alkyl sulfone group are excluded.

2. An emitting compound selected from the group consisting of following Formulas 2, 4, 5, 7-10 and 12 -31:

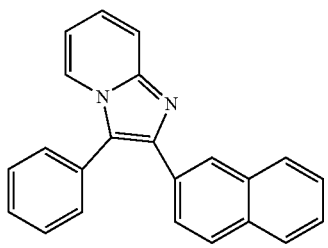
Formula 2
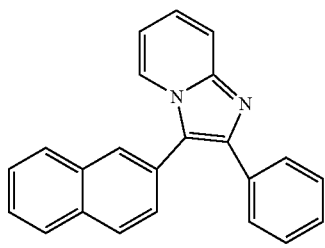
Formula 4
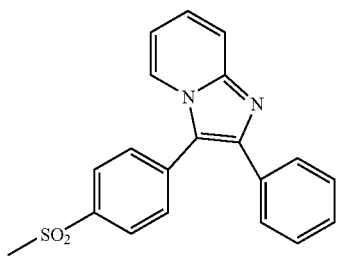
Formula 5
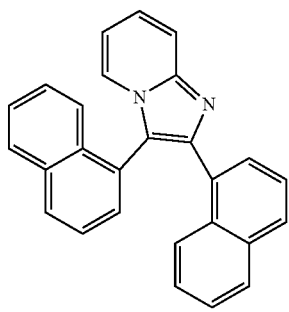
Formula 7
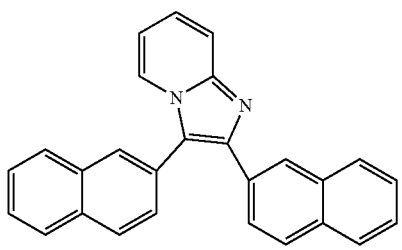
Formula 8
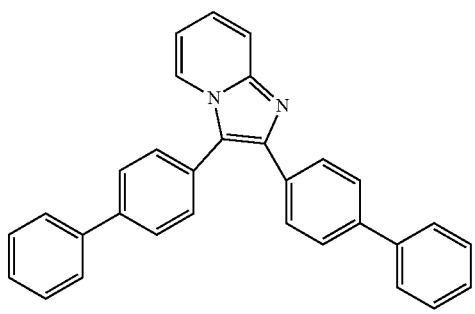
Formula 9
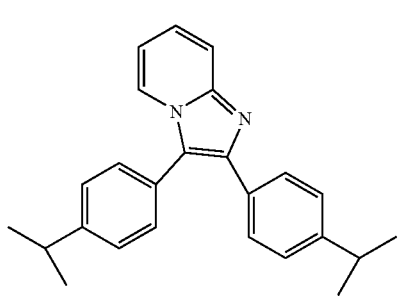
Formula 10
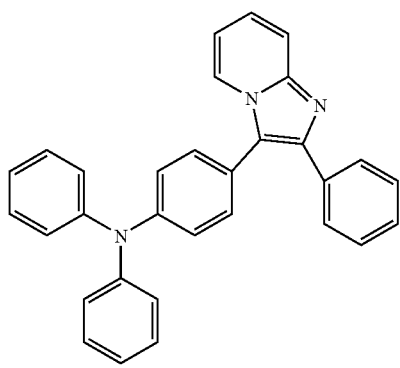
Formula 12

-continued
Formula 13
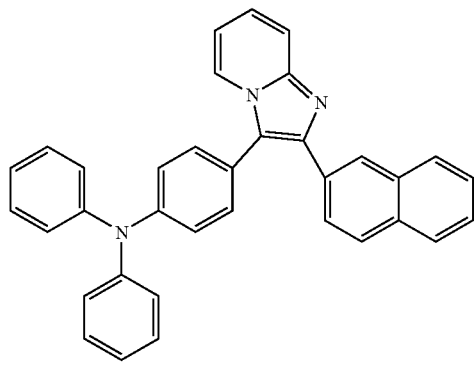
Formula 14
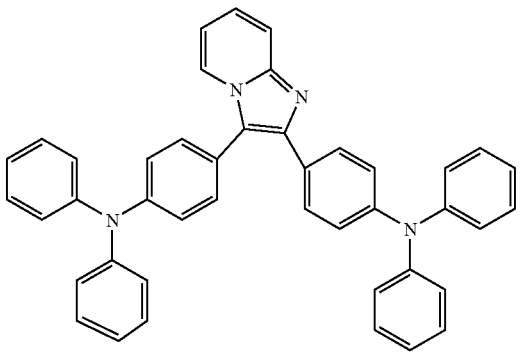
Formula 15
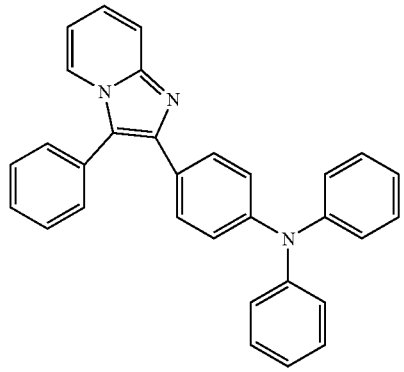
Formula 16
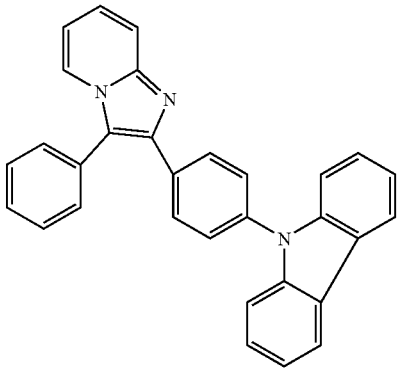
Formula 17
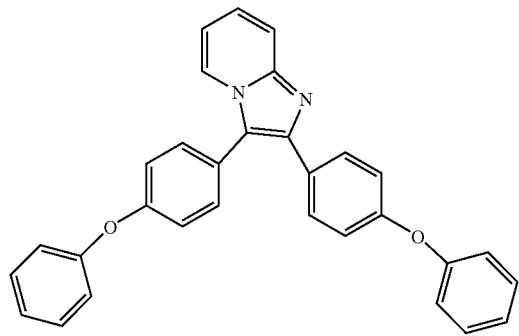
Formula 18
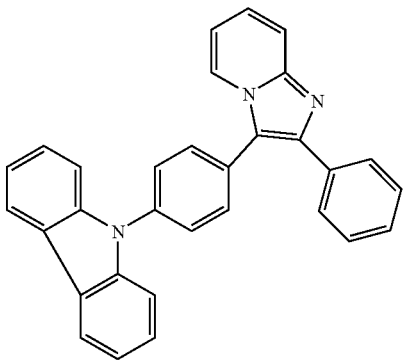
Formula 19
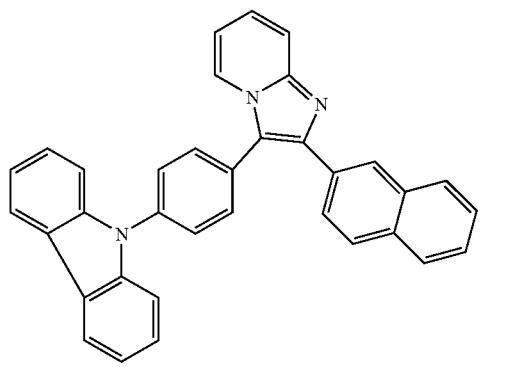
Formula 20
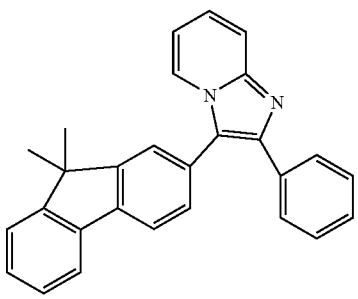

-continued
Formula 21
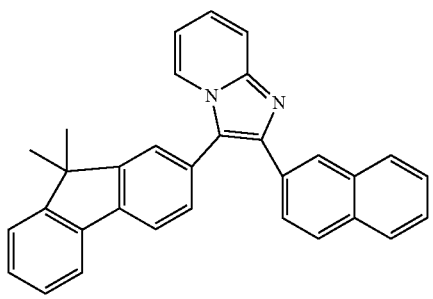
Formula 22
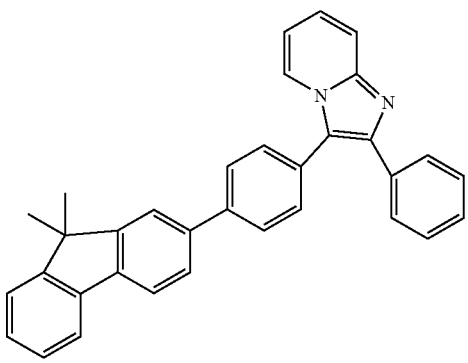
Formula 23
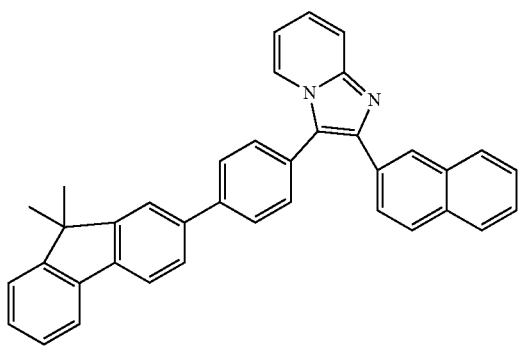
Formula 24
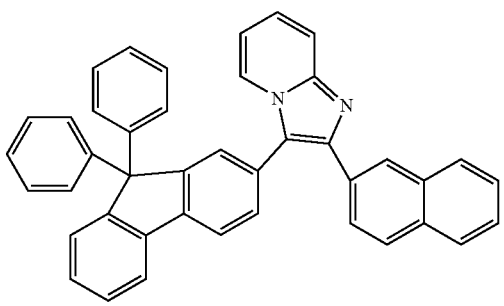
Formula 25
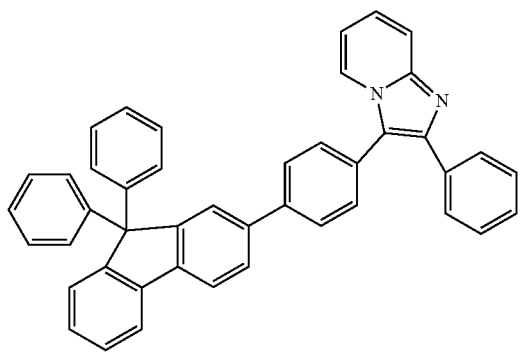
Formula 26
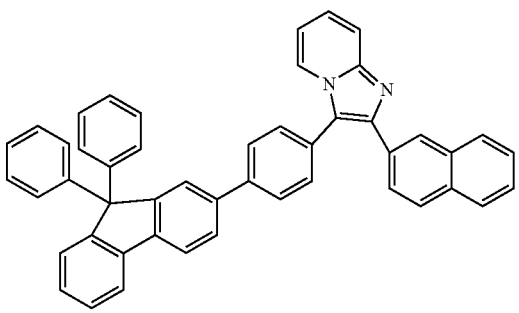
Formula 27
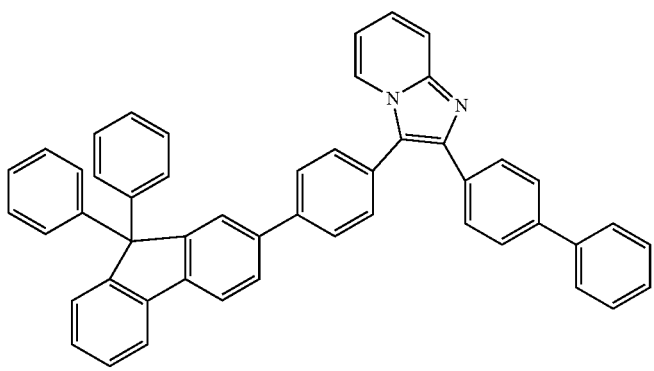

-continued
Formula 28
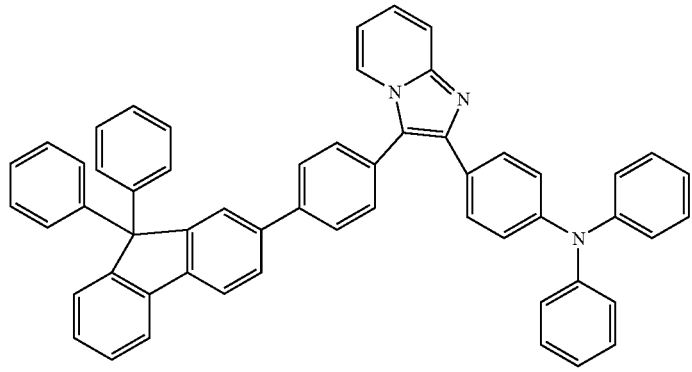
Formula 29
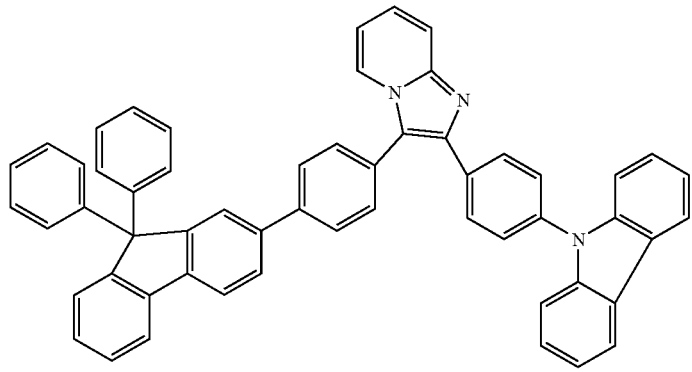
Formula 30
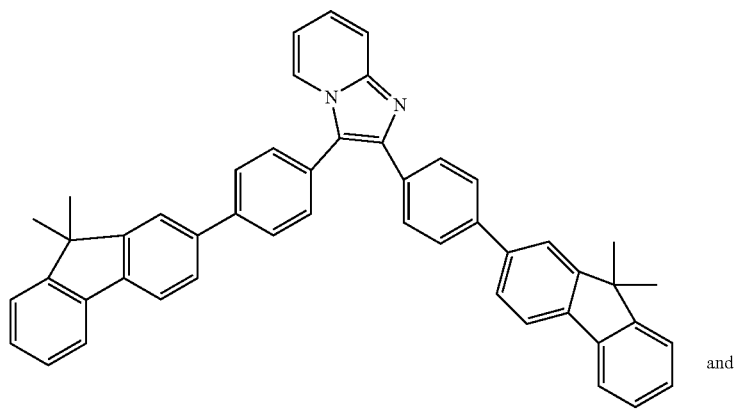
and
Formula 31
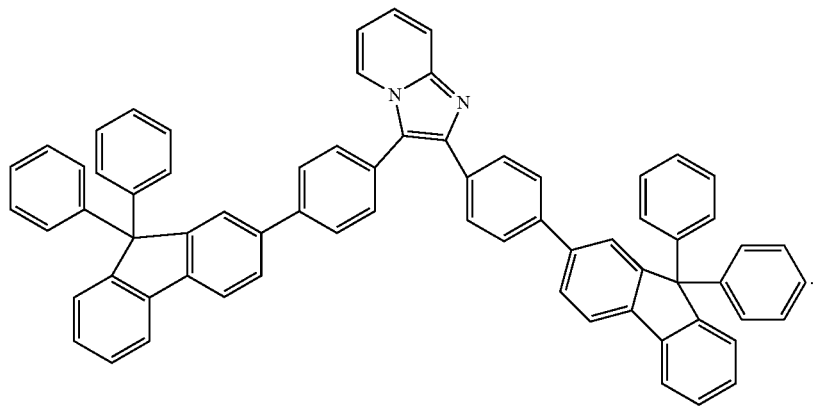

3. The emitting compound according to claim 1, wherein the compound represented as in Formula 1 is a blue emitting compound.

4. An organic electroluminescent device comprising:
a pair of electrodes; and
an organic compound layer formed in at least one layer and having an emitting layer positioned between the electrodes and comprising a compound represented as in the following Formula 1:

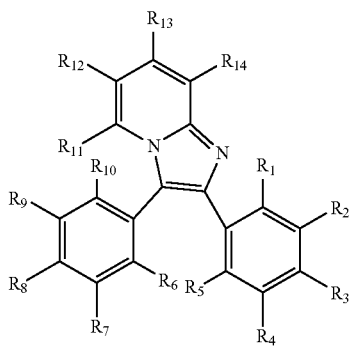

Formula 1 where $R_1$ to $R_{14}$, each of which is independent, are each one functional group selected from the group consisting of a hydrogen atom, a halogen atom, a substituted or a non-substituted alkyl group having 1 to 30 carbon atoms, a substituted or a non-substituted alkoxy group having 1 to 30 carbon atoms, a substituted or a non-substituted aryl group having 6 to 30 carbon atoms, a substituted or a non-substituted aryloxy group having 6 to 30 carbon atoms, a substituted or a non-substituted heterocyclic group having 6 to 30 carbon atoms, a substituted or a non-substituted condensation polycyclic group having 6 to 30 carbon atoms, a substituted or a non-substituted heterocyclic group having 5 to 30 carbon atoms, an amino group, an arylamino group having 6 to 30 carbon atoms, a cyano group, a nitro group, a hydroxy group, an aryl sulfone group having 6 to 30 carbon atoms, an alkyl sulfone group having 1 to 30 carbon atoms, and a group that is bonded to an adjacent group of $R_1$ to $R_{14}$ to form a saturated or a nonsaturated carbon ring, and wherein the case of $R_1$ to $R_{10}$ all being hydrogens and the case of any one of $R_1$ to $R_{14}$ being methyl, ethyl, $OCH_3$ or imidazopyridine are excluded.

5. An organic electroluminescent device comprising:
a pair of electrodes; and
an organic compound layer formed in at least one layer and having an emitting layer positioned between the electrodes and comprising a compound selected from the group consisting of following Formulas-2,4,5,7-10 and 12-31:

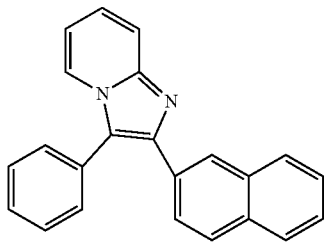

Formula 2

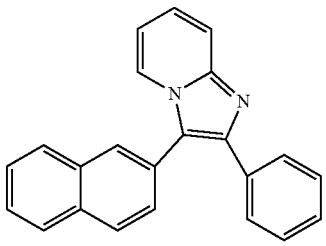

Formula 4

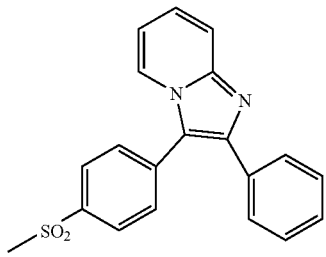

Formula 5

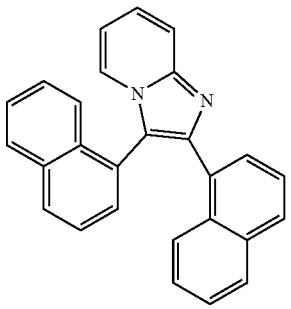

Formula 7

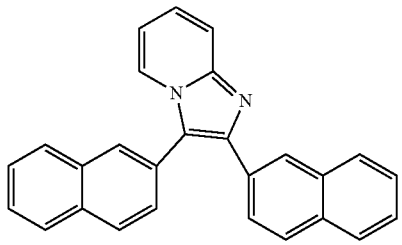

Formula 8

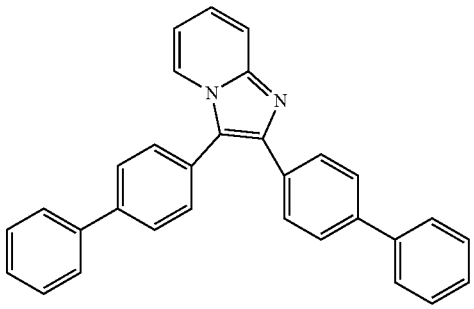

Formula 9

-continued
Formula 10
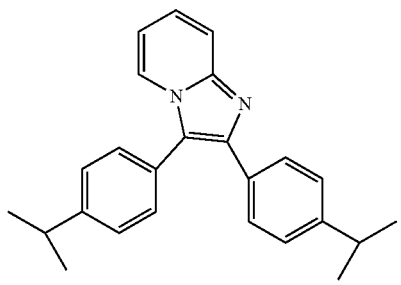
Formula 12
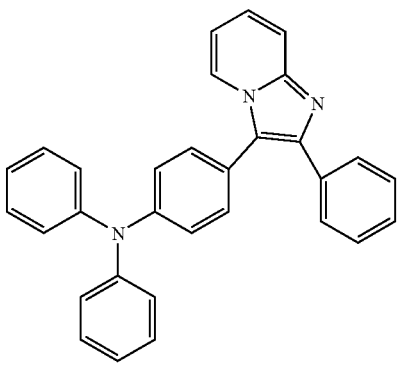
Formula 13
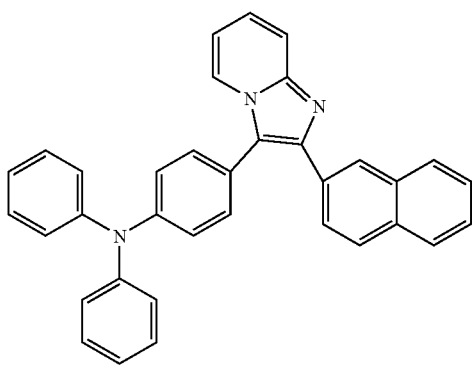
Formula 14
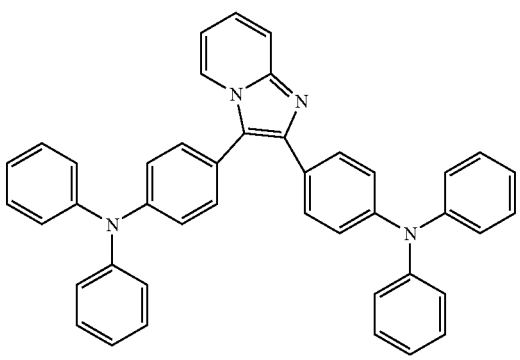
Formula 15
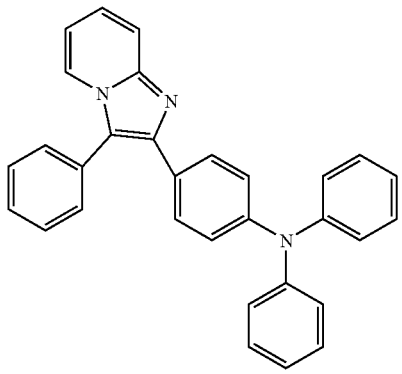
Formula 16
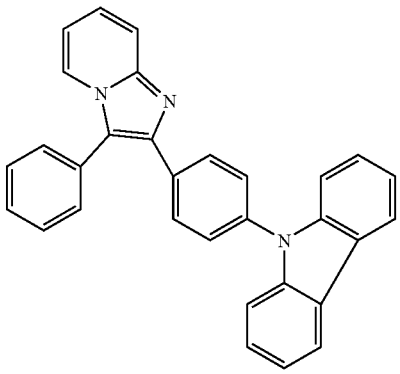
Formula 17
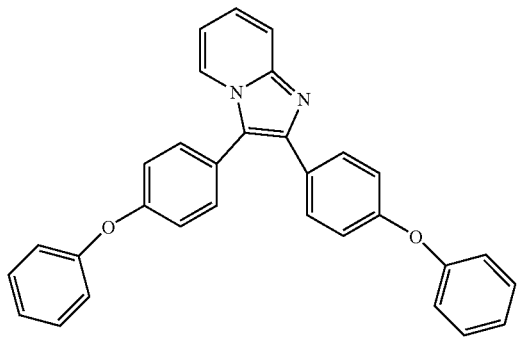
Formula 18
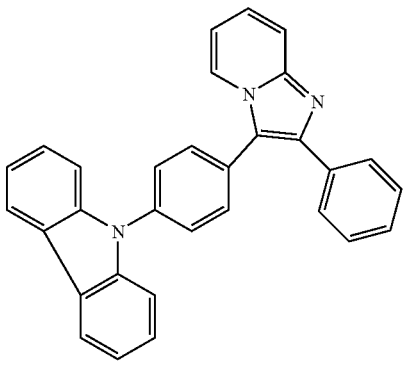

-continued
Formula 19
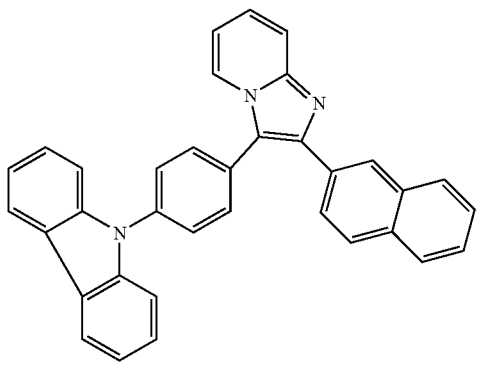
Formula 20
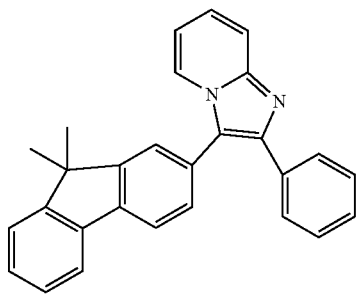
Formula 21
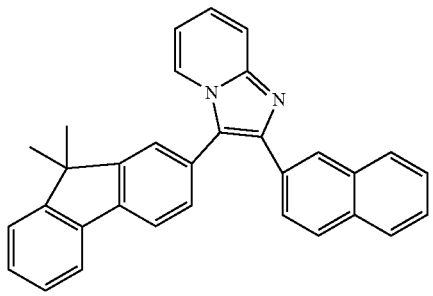
Formula 22
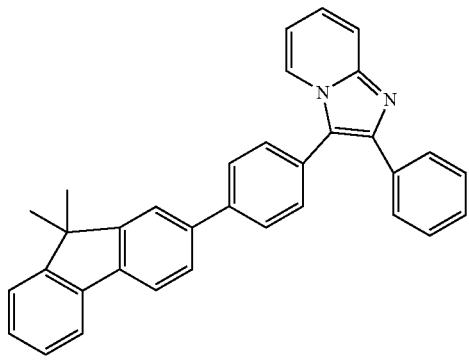
Formula 23
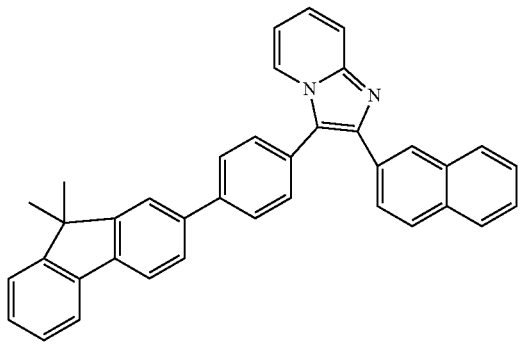
Formula 24
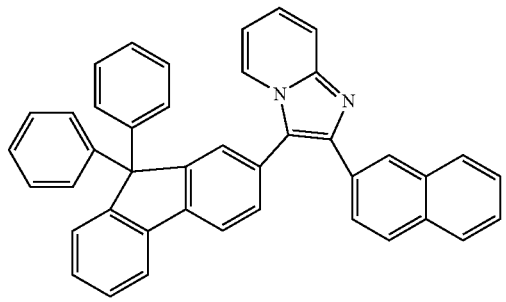
Formula 25
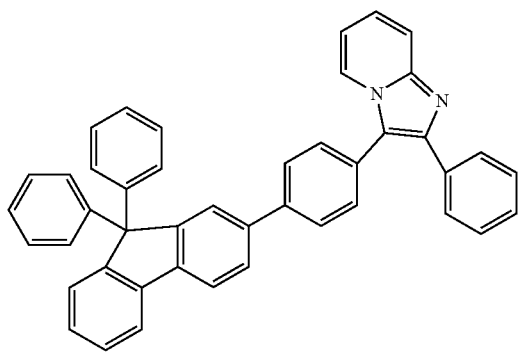
Formula 26
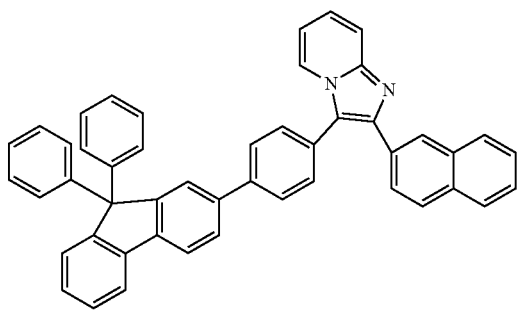

Formula 27
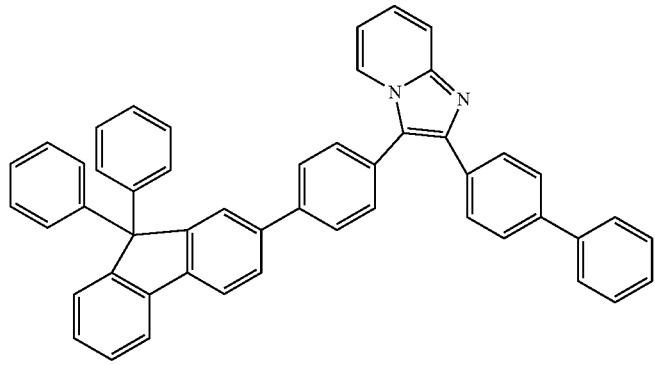
Formula 28
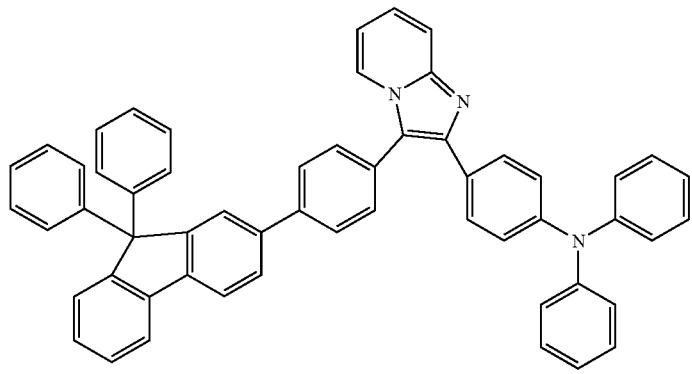
Formula 29
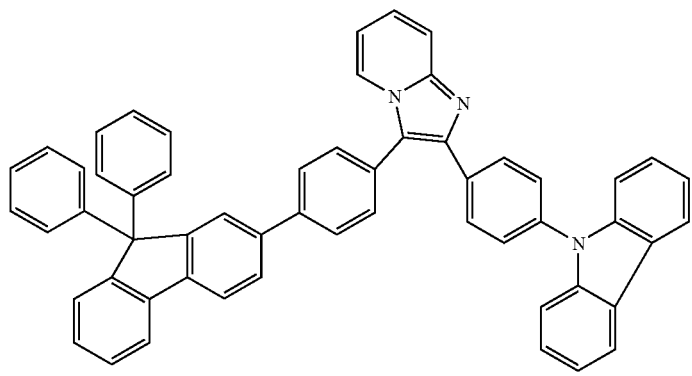
Formula 30
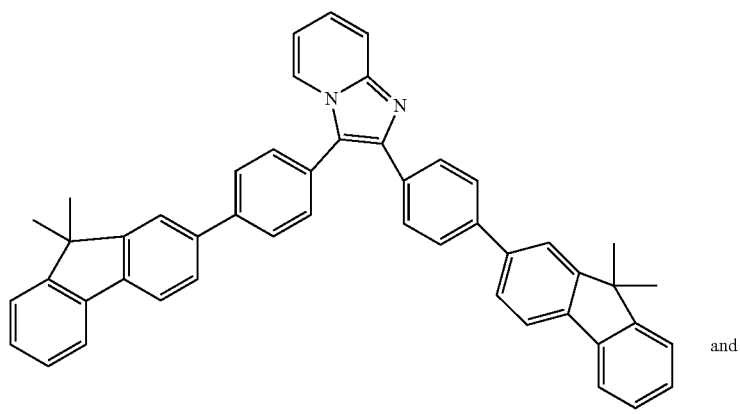
and -continued

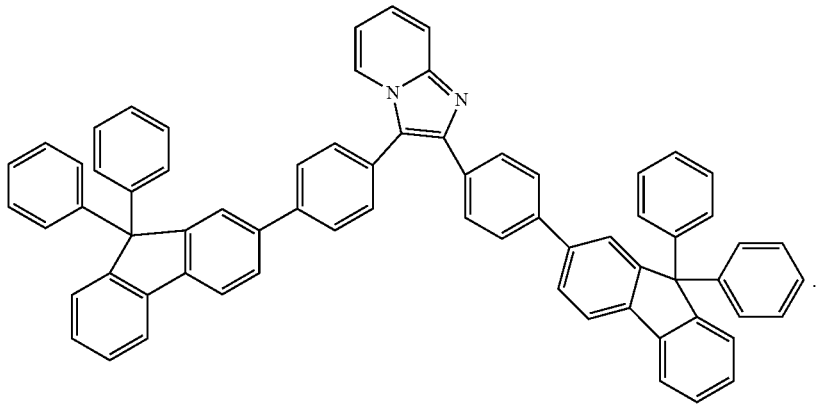

Formula 31

6. The organic electroluminescent device according to claim 4, wherein the compound of Formula 1 is a blue emitting compound.

7. The organic electroluminescent device according to claim 4, wherein the emitting layer further comprises one of a blue phosphorescent dopant and a fluorescent dopant.

8. The organic electroluminescent device according to claim 4, wherein the organic compound layer comprises at least one layer selected from the group consisting of a hole injection layer, a hole transport layer, an electron injection layer, and an electron transport layer.

* * * * *

UNITED STATES PATENT AND TRADEMARK OFFICE
CERTIFICATE OF CORRECTION

PATENT NO.      : 7,632,578 B2
APPLICATION NO. : 10/770445
DATED           : December 15, 2009
INVENTOR(S)     : Seok-Jong Lee et al.

Page 1 of 1

It is certified that error appears in the above-identified patent and that said Letters Patent is hereby corrected as shown below:

Column 36, line 1, insert

-- Formula 14

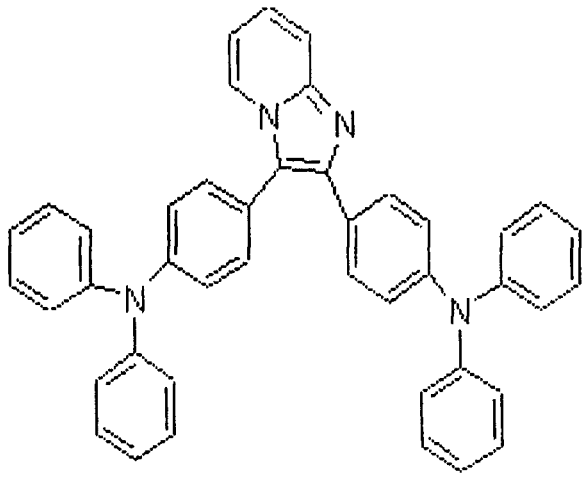

--.

Signed and Sealed this

Twenty-third Day of March, 2010

David J. Kappos
*Director of the United States Patent and Trademark Office*

UNITED STATES PATENT AND TRADEMARK OFFICE
CERTIFICATE OF CORRECTION

PATENT NO. : 7,632,578 B2  Page 1 of 1
APPLICATION NO. : 10/770445
DATED : December 15, 2009
INVENTOR(S) : Lee et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 631 days.

Signed and Sealed this

Twenty-first Day of December, 2010

David J. Kappos
*Director of the United States Patent and Trademark Office*